United States Patent
Kawarai et al.

(10) Patent No.: US 12,109,430 B2
(45) Date of Patent: Oct. 8, 2024

(54) ANIMAL TREATMENT APPARATUS, PHOTOTHERAPEUTIC APPARATUS, AND ANIMAL TREATMENT METHOD

(71) Applicant: NICHIA CORPORATION, Anan (JP)

(72) Inventors: Shinpei Kawarai, Sagamihara (JP); Atsushi Tsukamoto, Sagamihara (JP); Shota Kubota, Sagamihara (JP); Yasuo Fujikawa, Yokohama (JP); Tomohiro Tsurumoto, Yokohama (JP); Makiko Yamagishi, Azumino (JP)

(73) Assignee: NICHIA CORPORATION, Anan (JP)

( * ) Notice: Subject to any disclaimer, the term of this patent is extended or adjusted under 35 U.S.C. 154(b) by 649 days.

(21) Appl. No.: 17/243,865

(22) Filed: Apr. 29, 2021

(65) Prior Publication Data

US 2021/0275826 A1 Sep. 9, 2021

Related U.S. Application Data

(63) Continuation of application No. PCT/JP2019/042636, filed on Oct. 30, 2019.

(30) Foreign Application Priority Data

Oct. 31, 2018 (JP) ................................ 2018-206015
Jul. 29, 2019 (JP) ................................ 2019-139154

(51) Int. Cl.
*A61N 5/06* (2006.01)
*A61D 1/00* (2006.01)

(52) U.S. Cl.
CPC .... *A61N 5/0616* (2013.01); *A61N 2005/0626* (2013.01); *A61N 2005/0652* (2013.01); *A61N 2005/0661* (2013.01)

(58) Field of Classification Search
CPC .......... A61N 5/0616; A61N 2005/0626; A61N 2005/0652; A61N 2005/0661; A61N 2005/0644; A61D 1/00
See application file for complete search history.

(56) References Cited

U.S. PATENT DOCUMENTS 5,344,433 A * 9/1994 Talmore ................ A61N 5/062
607/88
6,596,016 B1 * 7/2003 Vreman ............... A61N 5/0621
128/903

(Continued)

FOREIGN PATENT DOCUMENTS

JP S52-089875 U1 7/1977
JP 2007-267936 A 10/2007

(Continued)

OTHER PUBLICATIONS

Mochizuki T, Iwasaki T. Minimal erythema dose (MED) in normal canine skin by irradiation of narrow-band ultraviolet B (NB-UVB). J Vet Med Sci. Jan. 31, 2013;75(1):119-21. doi: 10.1292/jvms.12-0212. Epub Oct. 10, 2012. PMID: 22971723. (Year: 2012).*

(Continued)

*Primary Examiner* — Lynsey C Eiseman
*Assistant Examiner* — Christopher J Mutchler
(74) *Attorney, Agent, or Firm* — Foley & Lardner LLP

(57) ABSTRACT

A method of treating a non-human animal subject includes irradiating, one or more times, light having a peak wavelength in a range of 315-335 nm to an affected area of the animal subject.

15 Claims, 18 Drawing Sheets

(56) References Cited

U.S. PATENT DOCUMENTS

| | | | |
|---|---|---|---|
| 2004/0075065 A1* | 4/2004 | Spivak | A61N 5/0614 250/504 R |
| 2006/0206173 A1* | 9/2006 | Gertner | A61N 5/0616 607/88 |
| 2006/0271132 A1* | 11/2006 | Fiset | B82Y 20/00 607/94 |
| 2007/0233210 A1 | 10/2007 | Morita et al. | |
| 2008/0281385 A1 | 11/2008 | Inada et al. | |
| 2009/0093799 A1* | 4/2009 | Davenport | A61N 5/0616 606/9 |
| 2012/0059441 A1* | 3/2012 | Chang | A61N 5/0616 607/90 |
| 2014/0323950 A1 | 10/2014 | Wirth | |
| 2017/0361125 A1 | 12/2017 | Lakios et al. | |
| 2019/0168017 A1 | 6/2019 | Morita et al. | |

FOREIGN PATENT DOCUMENTS

| | | |
|---|---|---|
| JP | 2008-528188 A | 7/2008 |
| JP | 2008-539808 A | 11/2008 |
| JP | 2014-532672 A | 12/2014 |
| JP | 2017-047219 A | 3/2017 |
| JP | 2017-510342 A | 4/2017 |
| JP | 2018-086108 A | 6/2018 |
| WO | WO-2006/081312 A2 | 8/2006 |
| WO | WO-2006/099413 A2 | 9/2006 |
| WO | WO-2007/066657 A1 | 6/2007 |
| WO | WO-2015/130891 A2 | 9/2015 |
| WO | WO-2018/142630 A1 | 8/2018 |

OTHER PUBLICATIONS

Xin Hongzhen, "Fundamentals of Photometry, Colormetry;" Global Efficient Lighting Centre; 2017 (Year: 2017).*

Roy A. Palmer, Susan Aquilina, Peter J. Milligan, Susan L. Walker, John L.M. Hawk, Antony R. Young; "Photoadaptation during Narrowband Ultraviolet-B Therapy Is Independent of Skin Type: A Study of 352 Patients;" Journal of Investigative Dermatology, vol. 126, Issue 6, pp. 1256-1263, (Year: 2006).*

Tatjana Haitina, Robert Fredriksson, Steven M Foord, Helgi B Schiöth, and David E Gloriam; "The G protein-coupled receptor subset of the dog genome is more similar to that in humans than rodents;" BMC Genomics 2009, 10:24; Published: Jan. 15, 2009 (Year: 2009).*

Hydar Ali, "Mas-Related G Protein Coupled Receptor-X2: A Potential New Target for Modulating Mast Cell-Mediated Allergic and Inflammatory Diseases;" Journal of Immunobiology, vol. 1, Issue 4; Dec. 28, 2016 (Year: 2016).*

Burhan Engin, Mustafa Özdemir, Ali Balevi and Inci Mevlitoğlu; "Treatment of Chronic Urticaria with Narrowband Ultraviolet B Phototherapy: a Randomized Controlled Trial;" Acta Derm Venereol 2008; vol. 88, Issue 3, pp. 247-251 (Year: 2008).*

Fujisawa et al., "Expression of Mas-related gene X2 on mast cells is upregulated in the skin of patients with severe chronic urticaria", The Journal of Allergy and Clinical Immunology, Sep. 2014, pp. 622-633, vol. 134, No. 3.

Hisatomi et al., "Toxicity of Polyoxyethylene Hydrogenated Castor Oil 60 (HCO-60) In Experimental Animals", The Journal of Toxicological Sciences, 1993, pp. 1-9, vol. 18, Supplement III.

McNeil et al., "Identification of a mast-cell-specific receptor crucial for pseudo-allergic drug reactions", NATURE, Mar. 12, 2015, pp. 237-241, vol. 519, Macmillan Publishers Limited.

Nimmo Wilkie et al., "Morphometric Analyses of the Skin of Dogs with Atopic Dermatitis and Correlations with Cutaneous and Plasma Histamine and Total Serum IgE", Veterinary Pathology, 1990, pp. 179-186, vol. 27.

Sugiyama et al., "Canine skin mast cell degranulation from polyoxyethylene hydrogenated castor oil 60 containing human drugs", Veterinary Dermatology, 2016, p. 76.

Tatemoto et al., "Immunoglobulin E-independent activation of mast cell is mediated by Mrg receptors", Biochemical and Biophysical Research Communications, 2006, pp. 1322-1328, vol. 349, Elsevier Inc.

Theerawatanasirikul et al., "Histologic morphology and involucrin, filaggrin, and keratin expression in normal canine skin from dogs of different breeds and coat types", Journal of Veterinary Science, 2012, pp. 163-170, vol. 13, No. 2, The Korean Society of Veterinary Science.

* cited by examiner

Minimal Erythema Dose Tests

|       | 310nm        | 320nm                        |
|-------|--------------|------------------------------|
| Dog A | 800mJ/cm$^2$ | —                            |
| Dog B | 1500mJ/cm$^2$ | —                           |
| Dog C | 400mJ/cm$^2$ | —                            |
| Dog D | 1500mJ/cm$^2$ | No Erythema at 1500mJ/cm$^2$ |
| Dog E | 400mJ/cm$^2$ | No Erythema at 1500mJ/cm$^2$ |

*Figure 15*

Allergic Reaction Inhibiion Tests

|  |  | Allergen | |
| --- | --- | --- | --- |
|  |  | Low Conc. | High Conc. |
| Repeated measure analysis of variance | All goups | $p < 0.01$ | No significance |
| Dunntt's t-test | 310nm | $p < 0.01$ | No significance |
|  | 320nm | $p < 0.01$ | $p < 0.05$ |
|  | 330nm | $p < 0.01$ | No significance |

*Figure 17*

| Times | Dose | Irradiation Time |
|---|---|---|
| 1 | 300mJ/cm² | 46sec |
| 2 | 400mJ/cm² | 62sec |
| 3 | 500mJ/cm² | 77sec |
| 4 | 600mJ/cm² | 93sec |
| 5 | 700mJ/cm² | 108sec |
| 6 | 800mJ/cm² | 123sec |
| 7 | 800mJ/cm² | 123sec |

ANIMAL TREATMENT APPARATUS, PHOTOTHERAPEUTIC APPARATUS, AND ANIMAL TREATMENT METHOD

CROSS-SECTION TO RELATED APPLICATIONS

The present application is a bypass continuation of PCT Application No. PCT/JP2019/042636, filed on Oct. 30, 2019, which claims priority to Japanese Application No. 2018-206015, filed on Oct. 31, 2018, and Japanese Application No. 2019-139154, filed on Jul. 29, 2019. These applications are incorporated by reference in their entireties.

BACKGROUND

The present disclosure relates to an animal treatment apparatus, a phototherapeutic apparatus, and an animal treatment method, for treating skin diseases or disorders, for example.

Japanese Patent Application Laid-Open (KOKAI) Publication No. 2007-267936 discloses a phototherapy device for irradiation of diseased sites with therapeutic irradiation with a spectrum in the UV-B irradiation wavelength range that is continuous at least in the wavelength range of 303 nm or less and has a lower limit of 297 nm or more. The phototherapy device has a light source emitting light with a spectrum that has an emission peak in the wavelength range from 300 nm to 315 nm and that is continuous at least in the wavelength range of 295 nm or less to the emission peak wavelength; and an irradiation emission window in which the light from the light source is incident and via which the therapeutic irradiation is emitted with a spectrum with a lower limit of 297 nm to 303 nm.

Human epidermis is 0.2 mm thick on average and is composed of 8-14 layers of cells, while canine and feline epidermis has a thickness of 0.2 mm or less and is composed of 2 or 3 layers of nucleated cells (Textbook of Modern Dermatology, Hiroshi Shimizu, Nakayama Shoten; Muller and Kirk's Small Animal Dermatology, W. Miller, C. Griffin, and K. Campbell, 7th eds. Elsevier; and Theerawatanasirikul S., et al., J. Vet. Sci., 13(2): 163-70, 2012). The difference raises concerns that irradiation of non-human animal skin with the light for treatment of human skin may cause an adverse reaction, such as erythema.

Certain embodiments of the present disclosure aim to provide an animal treatment apparatus or the like, which causes less side reaction to non-human animals as compared to the case of irradiating the animals with the light used for treating humans.

An apparatus for treating an animal subject according to one embodiment comprises: a light source capable of emitting light having a peak wavelength in a range of 315-335 nm that irradiates the animal subject; and a support member configured to support the light source.

A phototherapeutic apparatus according to one embodiment comprises: a light emitting unit capable of emitting first light having a peak wavelength in a range of 305 to 315 nm and second light having a peak wavelength in a range of 315-335 nm that irradiate an affected area; and a controller configured to switch the light to that irradiates the affected area between the first light and the second light.

A method of treating a non-human animal subject according to one embodiment comprises a step of irradiating, one or more times, light having a peak wavelength in a range of 315-335 nm to an affected area of the animal subject.

A method of treating a non-human animal subject according to one embodiment comprises: a first step of irradiating a skin of the animal subject with light having a peak wavelength in a range of 315-335 nm at a predetermined irradiation dose; and a second step of irradiating the skin with the light irradiation in the first step at another irradiation dose that is a higher dose than the irradiation dose in the first step, or light having a shorter peak wavelength than the wavelength in the first step, one or more days after the irradiation in the first step.

According to the present invention, an animal treatment apparatus or the like can be provided, which causes less side reaction to non-human animals as compared to the case of irradiating the animals with the light used for treating humans.

BRIEF DESCRIPTION OF DRAWINGS

FIG. 15 is a table showing the results of minimal erythema dose tests.

FIG. 17 is a table showing the results of allergic reaction inhibition tests.

DETAILED DESCRIPTION

Figure 1:
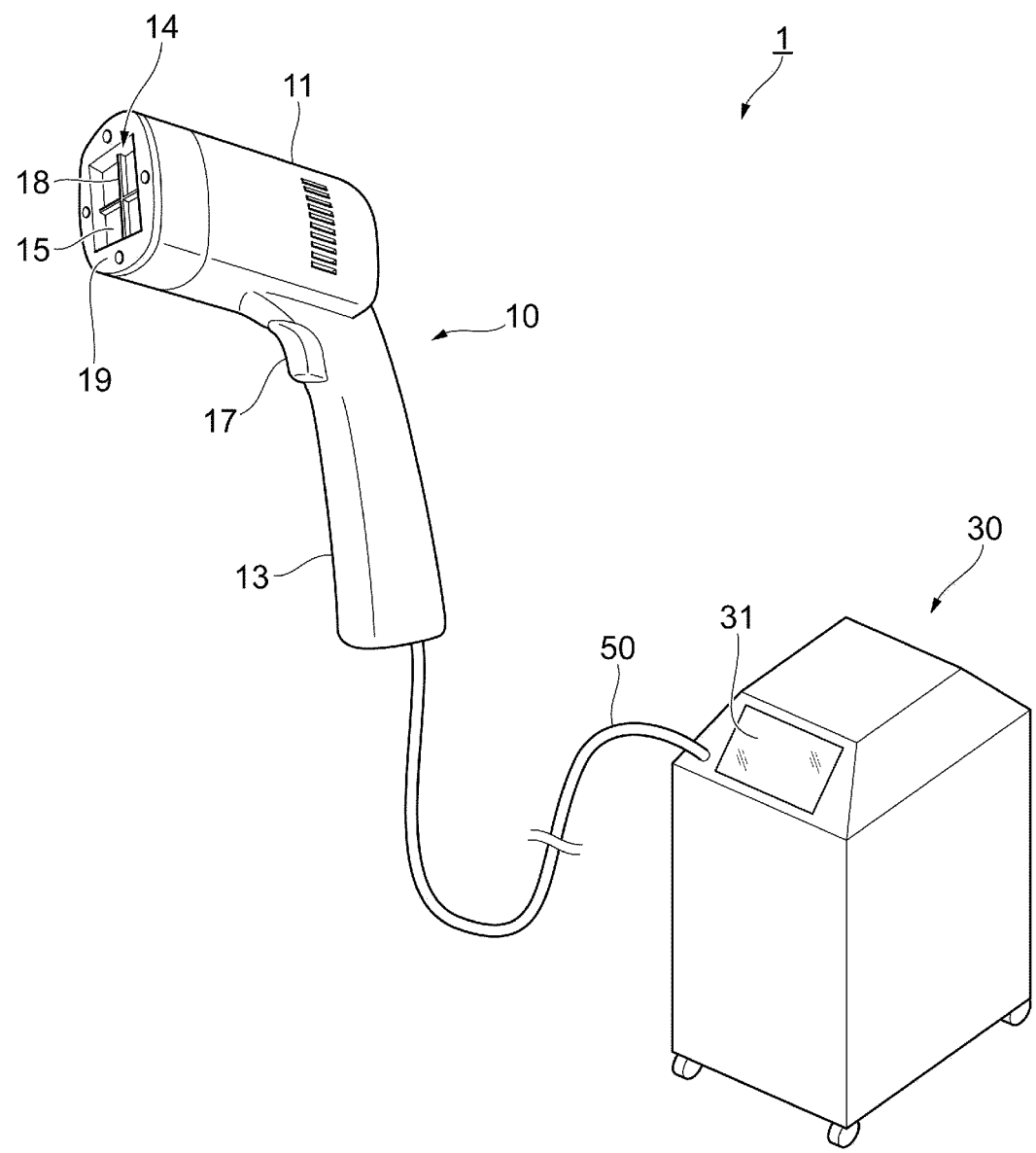
FIG. 1 is a schematic diagram of Embodiment 1 of an animal treatment apparatus according to the present invention.

As described in detail below, the present disclosure is based on a new finding that light having a peak wavelength in the range of 315-335 nm is effective in treating diseases or disorders in non-human animal subjects (such as dogs). The wavelengths of 315-335 nm are on the longer side than the wavelengths of 310 to 315 nm, at which light is said to be effective especially in humans, and are farther longer side than the wavelength 260 nm, at which light is easy to cause DNA (deoxyribonucleic acid) damage.

According to certain embodiments of the present invention, an animal treatment can be performed in a safe manner to the animal subject and the veterinarian performing the treatment.

<Animal Treatment Apparatus>

An animal treatment apparatus according to the present disclosure comprises at least one light-emitting unit that is capable of emitting light with a peak wavelength in the range of 315-335 nm.

(Light-Emitting Unit)

The light-emitting unit is capable of emitting a single light or a plurality of light, each having a peak wavelength in the range of 315-335 nm.

The light-emitting unit comprises at least one light source that is capable of emitting light with a peak wavelength in the range of 315-335 nm. The light sources may be supported by a support member.

The light source is not particularly limited so long as it is capable of emitting light having a peak wavelength in the range of 315-335 nm. Examples of the light source includes light emitting diodes (LEDs), laser diodes (LDs), halogen lumps, mercury lumps and the like, but a light emitting diode (LED) or a laser diode (LD) is particularly preferable. By the use of an LED or an LD, one can easily avoid irradiation with light at wavelength(s) that is not intended for the treatment. Due to the energy intensiveness, low heat generation, low power consumption and long life, use of an LED or an LD is preferable also in view of energy efficiency and economic efficiency. In addition, the illuminance or dose can be easily controlled or managed.

The light-emitting unit may comprise two or more light sources, such as an array, matrix or cluster of light sources. The light-emitting unit may comprise one or more light source modules, each composed of two or three types of light sources. The plurality of light sources or light source modules configuring the light-emitting unit may be individually controlled to light on and off. Such an individual control allows to reduce unwanted irradiation to non-irradiation area (normal areas, other than the affected area).

The light source included in the light-emitting unit may be a light source capable of emitting light having a peak wavelength in the range of 315-335 nm, so that the light-emitting unit is configured to be capable of emitting light having a peak wavelength in the range of 315-335 nm. In certain embodiments, therefore, the light-emitting unit may comprise a light source capable of emitting light having a peak wavelength in the range of 315-335 nm.

Alternatively, the light-emitting unit may emit light that have been extracted from the light emitted by a light source by using a member suppressing the transmission of light with the wavelength range of less than 315 nm and more than 335 nm, as the light having a peak wavelength in the range of 315-335 nm. In other embodiments, the light-emitting unit can comprise a light source that is capable of emit light with the wavelength range of 315-335 nm and a suppressing member to suppress the transmission of light of less than 315 nm and more than 335 nm, wherein the suppressing member is disposed in the path of the light emitted by the light source. Examples of the suppressing member include optical filters, such as cut-off filters.

The light-emitting unit emits light having a relative intensity at wavelengths less than 315 nm of, for example, 50% or less, preferably 40% or less, preferably 30% or less, more preferably 20% or less, more preferably 10% or less, more preferably 5% or less.

In embodiments wherein the relative intensity at wavelengths less than 315 nm is more than a desired value (such as the values mentioned above), the light-emitting unit may comprise a member suppressing the transmission of light of less than 315 nm in the path of the light emitted by the light source. The suppressing member for reducing the relative intensity at wavelengths less than 315 nm may also serve as a suppressing member to extract light having a peak wavelength in the range of 315-335 nm from the light emitted by a light source.

The light-emitting unit may be configured to be able to emit two or more kinds of light having peak wavelengths in the range of 315-335 nm, so that the light-emitting unit can emit one kind selected from the several kinds of light. A switch that switches the selected light on may be included in the light-emitting unit or provided outside thereof (in, for example, a controller as described below).

The two or more kinds of light having peak wavelengths in the range of 315-335 nm have the peak wavelengths in the respective consecutive sub-ranges of the range of 315-335 nm. One or more kinds of light having peak wavelengths in the range of 315-335 nm may be, for example, light having a peak wavelength in the range of 315-325 nm, or light having a peak wavelength in the range of 325-335 nm, or light having a peak wavelength in the range of 315-325 nm and light having a peak wavelength in the range of 325-335 nm.

For example, light having a peak wavelength in the range of 315-325 nm may have a peak wavelength at around 320 nm (for example, 320 nm±3 nm or 320 nm±1 nm) and light having a peak wavelength in the range of 325-335 nm may have a peak wavelength at around 330 nm (for example, 330 nm±3 nm or 330 nm±1 nm).

The light-emitting unit be configured to be able to emit light having a peak wavelength in the range of 305-315 nm in addition to one or more kinds of light having peak wavelengths in the range of 315-335 nm, so that the light-emitting unit can emit one kind selected from the several kinds of light. For example, light having a peak wavelength in the range of 305-315 nm may have a peak wavelength at around 310 nm (for example, 310 nm±3 nm or 310 nm±1 nm). A switch that switches the selected light on may be included in the light-emitting unit or provided outside thereof (in, for example, a controller).

The light-emitting unit may be able to emit one or more kinds of light having peak wavelengths in the range of 315-335 nm concurrently with light having a peak wavelength in the range of 305-315 nm.

The light-emitting unit capable of emitting two or more kinds of light may comprise light sources respectively corresponding to the kinds of light capable of being emitted, or may be configured to be capable of emitting the two or more kinds of light by a combination of a light source and a suppressing member. In the latter case, the light-emitting unit comprises a light source(s) in the number of which is less than the number of the kinds of light to be emitted and at least one suppressing member.

The animal treatment apparatus according to the present invention may comprise two or more light-emitting units. In this case, the plurality of light-emitting units may be individually controlled to turn the light on and off. Such an individual control to turn the light on and off makes it possible to reduce unwanted irradiation to non-irradiation area (normal areas, other than the affected area).

The light-emitting unit may be combined with any optical part(s) such as a lens(es), a reflector mirror(s), a mask(s), a light guide member(s) and/or a diffuser plate(s).

In the light-emitting unit that may be directly contacted with the animal, a transparent or light transmissive protective member may be provided on the light-emitting surface.

(Driver Unit)

The animal treatment apparatus according to the present invention may further comprise a driver unit to drive the light-emitting unit.

The driver unit may be composed of a driver circuit to drive the light-emitting unit. The driver unit is electrically connected to the light-emitting unit and provides power directly or indirectly to the light-emitting unit.

The driver unit can drive the light-emitting unit(s) to emit light according to the given emission conditions. Where the light-emitting unit comprises a plurality of light sources, the driver unit may drive only the selected light source(s) to emit light according to the given conditions.

The emission conditions include the wavelength, illuminance, lighting duration, lighting mode (continuous or intermitted light), pulse width, duty ratio and the like of light emitted by the light-emitting unit.

The emission conditions may be input to the driver unit via the control signals received directly from a controller as described below, or the control signals from a storage means (such as a memory), in which the emission conditions have previously stored. In certain embodiments, therefore, the driver unit comprises a storage.

The electric power may be supplied to the driver unit from the controller or from a battery. The battery may be chargeable and dischargeable and the battery may be charged with electric power supplied from the controller. In certain embodiments, the present animal treatment apparatus may further comprise: a driver unit that drives the light-emitting unit; and a battery holder that is capable of housing a battery (preferably a chargeable and dischargeable battery) to supply electric power to the driver unit. The battery appropriately housed in the battery holder can supply electric power to the driver unit. The supply of electric power to the driving unit may be achieved via a controller described below.

The driver unit is generally positioned in the vicinity or proximity of the light-emitting unit, but it may be located remotely from the light-emitting unit. The latter configuration increases the flexibility in the location of the light-emitting unit and therefore can provide various embodiments of the present treatment apparatus. For example, the driver unit may be provided in a housing together with the light-emitting unit, or in another housing that does not comprise the light-emitting unit.

The driver unit may comprise a switch that is operated by a use to switch on and off the light-emitting unit.

(Controller)

The animal treatment apparatus according to the present invention may further comprise a controller that control the driver unit.

The controller may be composed of a control circuit. The control circuit generates and outputs a control signal according to the emission conditions for the light-emitting unit, to the driver unit. The control circuit may comprise a pulse width modulation circuit and/or a timer. The controller may comprise a storage (such as a memory) that stores the irradiation conditions.

The controller may be electrically connected to the driver unit. More specifically, the controller may be constantly in electric connection to the driver unit, or may be connected to the driver unit when needed, via a pair of adaptors for example.

The controller may transmit a control signal regarding the emission conditions for the light-emitting unit, to the driver unit. The controller can also supply electric power to the driver unit or the chargeable and dischargeable battery (if applicable).

The controller may comprise an interface that receives an input of the emission conditions for the light-emitting unit. The interface may be a user interface (UI) that receives an input from a user or a communication interface. The emission conditions to be input via the interface may be stored in a storage device.

For example, the UI may be of a liquid crystal touch panel type or a switch type (a rotary switch(es) and/or a push switch(es)). The interface may not be in the proximity of the control circuit and may be located remotely therefrom. In particular, it is preferable if the UI is provided in the present treatment apparatus at the most accessible position for the user.

The communication interface may be, for example, a wireless interface such as infrared interface, Bluetooth™, near-field communication interface or the like.

In the embodiments wherein the light-emitting unit comprises a plurality of light source or wherein the present treatment apparatus comprises a plurality of light-emitting units (an array, matrix or cluster of light-emitting units), the controller can designate the light source or the light-emitting unit to emit light.

For example, the controller may be provided in a housing together with the driver unit, or in another housing that does not comprise the driver unit. The latter configuration increases the flexibility in the location of the light-emitting unit, or the locations of the light-emitting unit and the driver unit and therefore can provide various embodiments of the present treatment apparatus. Therefore, the present treatment apparatus can be provided in the form of grooming tools (for example, combs, brushes, gloves and the like), medical and sanitary devices (for example, tooth brushes and mouthpieces), playing toys, clothes and the like for animals.

The controller may further comprise a power source or a battery holder as needed. The power source may be, for example, an AC/DC adaptor or a battery (preferably chargeable and dischargeable battery).

In embodiments wherein the light-emitting unit is capable of simultaneously emitting one or more kinds of light having peak wavelengths in the range of 315-335 nm together with light having a peak wavelength in the range of 305-315 nm, the controller may control the respective light intensities so that the mixed light to be emitted has a relative intensity at wavelengths less than 315 nm of, for example, 50% or less.

(Other Components)

The present animal treatment apparatus may comprise a visible light source configured to be capable of irradiating substantially the same area as the one irradiated with the light having a peak wavelength in the range of 315-335 nm. According to these embodiments, users can easily and visibly confirm the area being irradiated with the (invisible) light having a peak wavelength in the range of 315-335 nm and thereby avoiding UV irradiation to unintended areas. As the visible light source, any known light source (for example, blue light source, green light source, red light source or white light source) can be used. The visible light source may be provided in, or separately from, the light-emitting unit. The visible light can be emitted simultaneously with, or separately from, the light having a peak wavelength in the range of 315-335 nm. The simultaneous emission allows the user to easily recognize that the light with a peak wavelength in the range of 315-335 nm is being emitted and therefore leads to increased safety.

The present treatment apparatus may comprise a holding or restraining mechanism to hold or restrain an animal. The holding or restraining mechanism is not particularly limited so long as it can restrict free movement of the animal to stay within a limited area. It is desirable that the holding or restraining mechanism does not cause fear or pain to the animal held or restrained thereby. The holding or restraining mechanism may be, for example, of a belt, harness or hammock type, or an enclosure (cage).

Because at least a part of the present animal treatment apparatus is directly touched by the animal or human hands touched by the animal, it is preferable that the part(s) is/are disinfected with sodium hypochlorite or ethanol for disinfection after every use. In view of sanitation, at least a part of the present animal treatment apparatus, which may be touched by the animal, is/are made of a chemical-resistant material(s).

DESCRIPTION OF SPECIFIC EMBODIMENTS

Hereinafter, embodiments of the present invention will be described in more detail with reference to the accompanying drawings as necessary.

Embodiment 1

Configuration of Animal Phototherapeutic Apparatus 1

FIG. 1 is a schematic diagram of an animal phototherapeutic apparatus 1.

Figure 2:
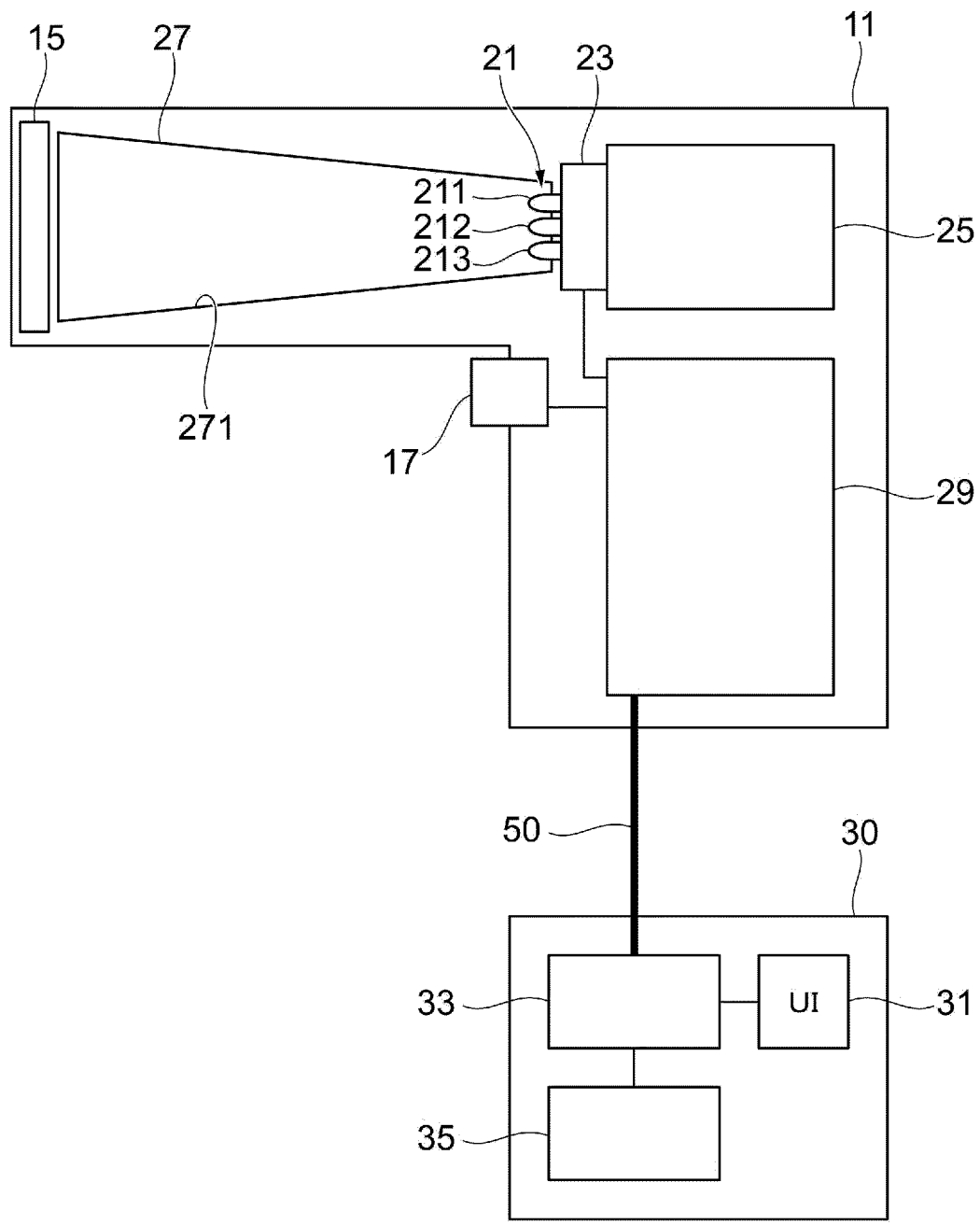
FIG. 2 is a block diagram of Embodiment 1.

FIG. 2 is a block diagram of the animal phototherapeutic apparatus 1.

The general configuration of the animal treatment apparatus 1 will be described below with reference to FIGS. 1 and 2.

The animal phototherapeutic apparatus 1 according to the present embodiment comprises an apparatus body 10, a controller 30 and a cable 50. The apparatus body 10, the controller 30 and the cable 50 are each described in detail below.

The apparatus body 10 emits light with wavelengths in a predetermined range(s). According to the present embodiment, the light emitted from the apparatus body 10 irradiates an animal subject to be treated. The apparatus body 10 as illustrated comprises a housing 11, a handle 13, an irradiation window 15, a switch 17 and a pressing surface 19.

The housing 11 accommodates therein functional component members such as light emitting diode(s) 21 (LED 21, described in detail below) that is a light source(s). The housing 11 has an opening 14 through which the light emitted by the LED 21 passes.

The handle 13 forms a part of the housing 11, which is gripped by a user such as a veterinarian. The user grips the handle 13 to direct the apparatus body 10 toward the animal subject for irradiation thereof. More specifically, the apparatus body 10 as illustrated can be directed in any direction according to an affected area to be treated of the animal subject.

The irradiation window 15 is a covering member to cover the opening 14 provided in the housing 11. The irradiation window 15 is composed of a cover glass or the like that can transmit the light emitted by the LED 21 positioned inside the housing 11. The opening 14 and the irradiation window 15 as illustrated each have a substantially rectangular shape in a planar view but are not limited thereto. The irradiation window 15 as illustrated is supported by a frame member 18 provided on the outer surface of the irradiation window 15.

The switch 17 protrudes from the outer surface of the housing 11. The switch 17 is configured to switch on and off the LED 21 when pushed by the user.

The pressing face 19 forms a part of the outer surface of the housing 11, which is pressed on the affected area or its vicinity of the animal subject. The pressing face 19 as illustrated is formed around the opening 14. By pressing the pressing face 19 on the affected area or the like of the animal, the distance between the LED 21 and the affected area is a predetermined distance. Thus, the user can locate the LED 21 relative to the area to be irradiated, by pressing the pressing face 19 on the affected area or the like of the animal subject.

The functional component members provided inside the housing 11 will be described below with reference to FIG. 2.

The housing 11 comprises therein the LED 21, an LED board 23, a cooling mechanism 25, a reflector 27 and an LED driver board 29.

The LED 21 is composed of a group of LEDs, which are different in emission wavelength from each other or one another. The LED 21 as illustrated is composed of a first LED 211, a second LED 212, a third LED 213. The first to third LEDs 211-213 emit light respectively having a peak wavelength at 310, 320 and 330 nm as described in detail below.

The LED board 23 is a circuit board on which the LED 21 is mounted. The LED board 23 supplies electric power to the LED 21 provided on the surface of the board.

The cooling mechanism 25 is provided on the LED board 23 and suppresses a rise in temperature of the LED 21 when the LED 21 emits light. The cooling mechanism 25 is composed of a heat sink, an air cooling fan or the like.

The reflector 27 reflects the light emitted from the LED 21 while focusing it onto an area to be irradiated, i.e., the affected area of the animal subject. The reflector 27 as illustrated is formed in the shape of inverted truncated cone, on the bottom surface of which the LED 21 is provided, and have an inner peripheral surface 271, which is inclined in such a manner that the inside dimension becomes larger as it is closer to the irradiation window 15.

The LED driver board 29 is a board configured to be electrically connected to the controller 30, the switch 17 and the LED board 23. The LED driver board 29 receives a control signal from the switch 17 and power from the controller 30, and supplies power to the LED 21 through the LED board 23. More particularly, when the switch 17 is on, the LED driver board 29 turns the LED 21 on under the irradiation conditions (described in detail below) set by the controller 30. When the switch 17 is off, the LED driver board 29 forcibly turns the LED 21 off. The LED driver board 29 also switches the LED to be lighted between the first LED 211, the second LED 212 and the third LED 213.

The LED driver board 29 may be electrically connected to the LED board 23 via a momentary switch, which is not illustrated. In the embodiments, the momentary switch is configured to be movable between an open position and a closed position in association with the movement of the pressing surface 19 (or a pressing member with a nozzle 300 as described below), while the pressing surface 19 (or the pressing member with the nozzle 300) is configured to be slidingly movable relative to the housing 11, substantially parallel to the optical axis of the LED 21 (or an axis from the LED 21 to the irradiated area of the animal), between a non-pressed position and a pressed position, in which the pressing surface 19 is being pressed on the affected area or the like of the animal. According to the embodiment, the LED 21 is lighted only when the pressing surface 19 (or the pressing member with the nozzle 300) is being pressed on the animal. Thus, with the apparatus according to the embodiment, there is no possibility of unwanted irradiation of other areas of the animal than the affected area, or the veterinary operating the apparatus or an assistant therefor, when the pressing surface 19 (or the pressing member with the nozzle 300) becomes separated from the animal due to its sudden movement or others and the opening 14 (or nozzle 305) is directed to other area than the affected area. Therefore, the safety of treatment farther improves.

Next, the controller 30 is described below. The controller 30 supplies electric power to the apparatus body 10. The controller 30 also can set the irradiation conditions for the LED 21. Specifically, the controller 30 can set the irradiation conditions including, for example, illuminance, irradiation time, lighting pattern (continuous lighting or pulse lighting), wavelength, pulse width, duty ratio and the like.

The controller 30 as illustrated comprises a user interface (UI) 31, a control board 33 and a power supply 35.

The UI 31 is composed of a liquid crystal panel or the like. The UI 31 is operated by the user to receive an input regarding the irradiation conditions, such as the wavelength(s) of the light emitted by the LED 21.

The control board 33 is connected to the UI 31 and the power supply 35 as well as to the LED driver board 29 in the apparatus body 10 via the cable 50. The control board 33 supplies the control signal according to the irradiation conditions received by the UI 31 and electric power from the power supply 35, to the LED driver board 29.

The power supply 35 supplies electric power to the control board 33 and any other components. The power supply 35 may be configured to directly connect to a home commercial power supply line (for example, 100 volts in countries such as Japan, 120 volts in countries such as the U.S., and 220 volts in countries such as China).

The cable 50 is a signal line(s) through which the control signal and electric power are transmitted between the apparatus body 10 and the controller 30. According to the illustrated embodiment, the apparatus body 10 receives electric power via the cable 50 even during the emission so that the apparatus body 10 can emit light for a longer time.

Emission Spectrum

Figure 3:
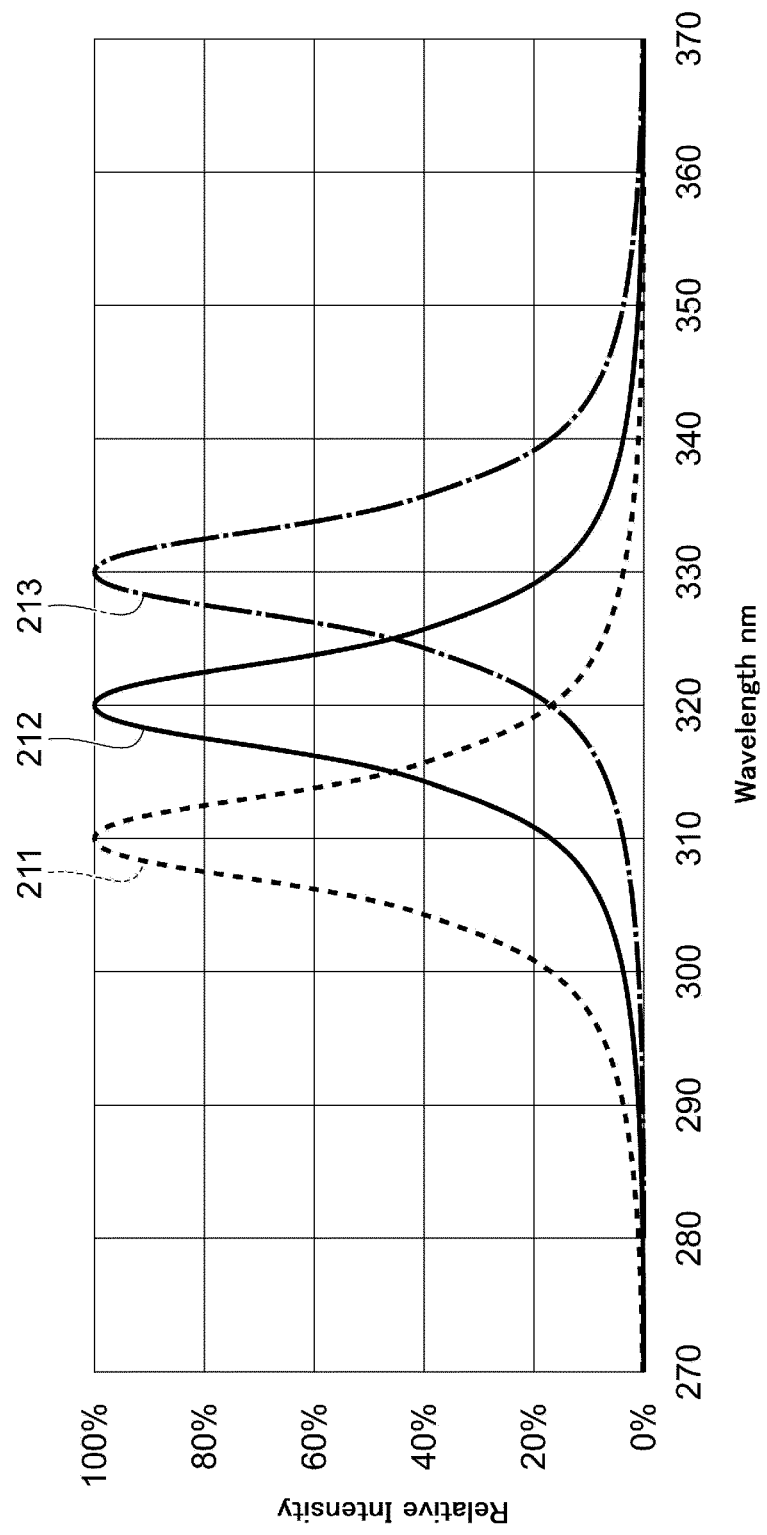
FIG. 3 shows the emission spectra of the LEDs used in the Experiment section.

FIG. 3 shows the emission spectra of the LED 21.

The emission spectra of the LED 21 will be described below with reference to FIGS. 2 and 3. As described above, the LED 21 comprises the first LED 211 to the third LED 213. The LEDs 211-213 all emit ultraviolet light, while the respective peak wavelengths of the light emitted by the LEDs 211-213 are different from one another. More specifically, the LEDs 211-213 respectively have peak wavelengths at around 310 nm, 320 nm and 330 nm as shown in FIG. 3.

The LED 211 has a peak wavelength in the range of 305-315 nm. The LED 212 has peak wavelength in the range of 315-325 nm. The LED 213 has peak wavelength in the range of 325-335 nm. Thus, the LEDs 211-213 are configured to have peak wavelengths in different limited ranges from one another.

The peak wavelength of the light emitted by the LED 21 varies according to the selection of the LED to be lighted among from these LEDs 211-213. More specifically, when any one of the LED 211, 212 or 213 is lighted on, the apparatus body 10 emits light having a peak wavelength at any one of 310, 320 or 330 nm. When two or three of the LEDs 211-213 are lighted on, the apparatus body 10 emits the light having the corresponding two or three peak wavelengths. When the second LED 212 and/or the third LED 213 is/are lighted on, the apparatus body 10 emits the light having a peak wavelength(s) in the range of 315-335 nm.

As the irradiation conditions for the LEDs 211-213 as illustrated, the pulse width and the duty ratio can be set, as described above. For example, the irradiation conditions are such that any one or more of the LEDs 211-213 emit pulsed light at a pulse width of 10 ms or less and a duty ratio of 10% or less. These irradiation conditions can reduce a rise in temperature of the irradiated area in the skin of the animal.

It is to be noted that the light emitted by the LEDs 211-213 is hereinafter also referred to simply as "310-nm light," "320-nm light" and "320-nm light," respectively.

Variations 1 and 2 of Embodiment 1

Figure 4:
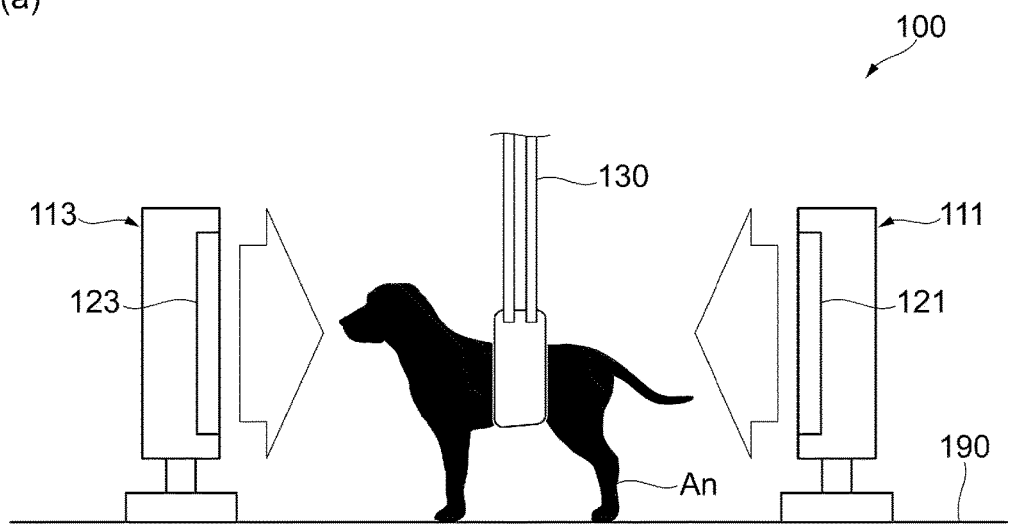
FIGS. 4(a) and 4(b) illustrate Variations 1 and 2 of Embodiment 1 of an animal treatment apparatus according to the present invention.
Figure 4:
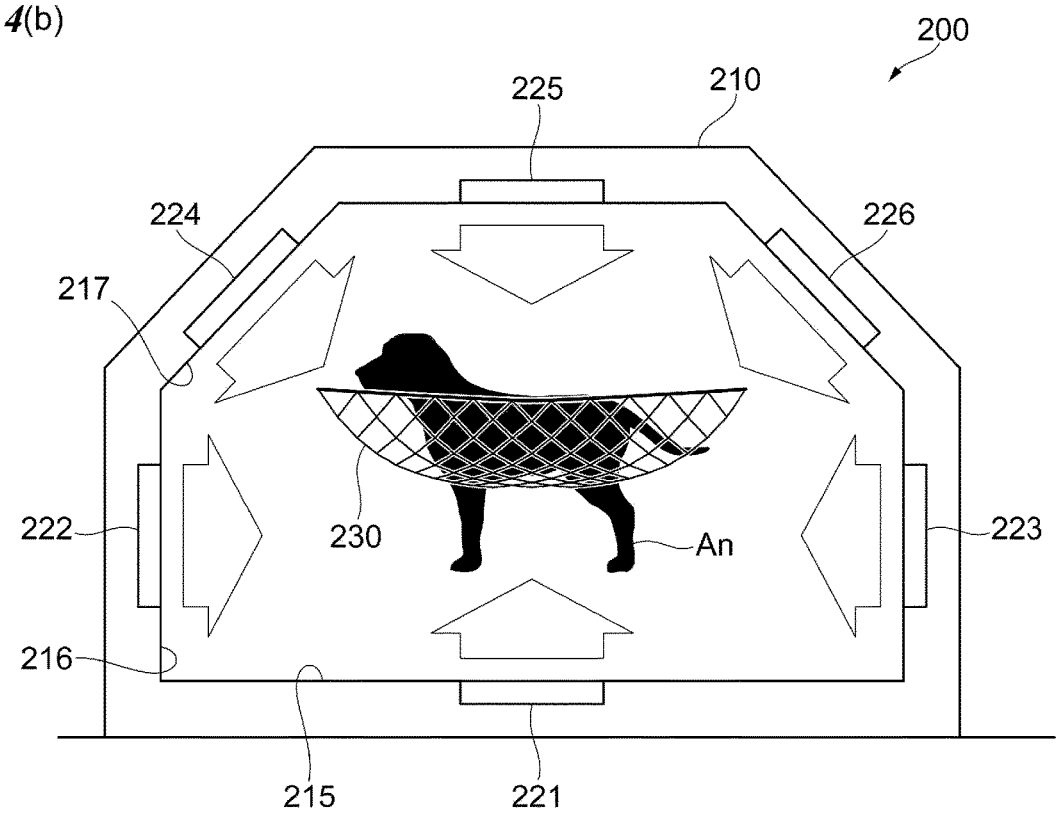

FIGS. 4(a) and 4(b) illustrate variations of the animal phototherapeutic apparatus 1.

The variations of the animal phototherapeutic apparatus 1 will be described below with reference to FIGS. 4(a) and 4(b).

The present apparatus is not limited to only those embodiments having a handy type apparatus body, such as the apparatus body 10 gripped by the user, as described previously.

For example, a variation may be an animal phototherapeutic apparatus 100 as illustrated in FIG. 4(a). The animal phototherapeutic apparatus 100 comprises a first irradiation unit 111, a second irradiation unit 113, and a restraining mechanism 130. The first irradiation unit 111 and the second irradiation unit 113 respectively comprise at least one first LED 121 and at least one second LED 123. The first irradiation unit 111 and the second irradiation unit 113, which are not gripped by the user, are placed on a floor 190. More specifically, the first irradiation unit 111 and the second irradiation unit 113 are arranged on the floor 190 so that a surface having the first LED 121 and a surface having the second LED 123 face each other. An animal An is positioned in the space between the first irradiation unit 111 and the second irradiation unit 113. The animal An is held and restrained by the restraining mechanism 130, which may be suspended from a ceiling for example.

The first LEDs 121 are two-dimensionally disposed on the first irradiation unit 111, and the second LEDs 123 are two-dimensionally disposed on the second irradiation unit 113. The first LED 121 and the second LED 123 are each capable of emitting the 310-nm light, the 320-nm light and the 330-nm light. The configuration can irradiate the light at predetermined wavelength(s) to a larger area, such as the whole body, of the animal An.

Another variation may be an animal phototherapeutic apparatus 200, which accommodates the animal An therein, as illustrated in FIG. 4(b). The animal phototherapeutic apparatus 200 comprises an accommodation unit 210, a first to a sixth LEDs 221-226, and a restraining mechanism 230. The accommodation unit 210 has an inner space for accommodating the animal An and a door (not illustrated) through which the animal An can be carried in the space. The first to sixth LEDs 221-226 are arranged on the inner surface of the accommodation unit 210. The accommodation unit 210 may be an intensive care box.

In a particular configuration, the first LED 221 is disposed in the accommodation unit 210 on a floor 215, the second LED 222 and the third LED 223 are disposed in the accommodation unit 210 on lateral surfaces 216, the fourth to sixth LEDs 214-216 are disposed in the accommodation unit 210 on ceiling plane(s) 271. The first to sixth LEDs 221-226 are each formed of a planer array of LEDs arranged on the inner surfaces (floor 215, lateral surfaces 216, and ceiling plane(s) 217) of the accommodation unit 210. The first to sixth LEDs 221-226 are capable of emitting 310-nm light, 320-nm light and 330-nm light. The configuration can irradiate the light at predetermined wavelength(s) to a larger area, such as the whole body, of the animal An.

The animal phototherapeutic apparatus 100 as illustrated in FIG. 4(a) can be referred to as an open-type apparatus wherein the animal An is positioned and treated in an open space. On the other hand, the animal phototherapeutic apparatus 200 as illustrated in FIG. 4(b) can be referred to as a closed-type apparatus wherein the animal An is positioned and treated in a closed space. In the case of using either type of apparatus, the animal An may wear eye protector glasses so as to reduce a risk of irradiating ultraviolet light to the eyes. The protector glasses may be in the form of goggle. As substitute for the protector glasses, protector members such as stickers may be put on the animal.

Previously, the animal phototherapeutic apparatus 100 as illustrated in FIG. 4(a) is described as including a harness-type restraining mechanism 130, and the animal phototherapeutic apparatus 200 as illustrated in FIG. 4(b) is described as including a hammock-type restraining mechanism 230. However, the restraining mechanism is not limited to the restraining mechanisms 130 and 230 as illustrated, as far as it can restrain the animal during the treatment. For example, a mechanism such as a cage (an enclosure) is used to restrain the animal An. The use of the restraining mechanism 130 or 230 restraining the animal An can save the effort by the user to hold the animal An during the treatment. Thus, the animal phototherapeutic apparatuses 100, 200 have less effect on the user and allow for easier treatment of animal.

The animal phototherapeutic apparatus 100 or 200 may comprise a distance-measuring device to measure the distances between the respective LEDs and the animal An. A controller, which is not illustrated, estimates the irradiation amount of the light emitted from the LED to the animal based on the measured distance, and increases or decreases the illuminance of the LED as appropriate. For example, the controller increases the illuminance of the LED when the distance between the LED and the animal is greater than the predefined value (i.e., when the irradiation amount of the LED is less than the predefined value), and decreases the illuminance of the LED when the distance between the LED and the animal is smaller than the predefined value (i.e., when the irradiation amount of the LED is more than the predefined value).

The irradiation amount may be confirmed by using an integrated light amount measured by an ultraviolet light amount distribution measuring film (for example, UV scale manufactured by FUJIFILM Corporation) attached to an animal.

Variation 3 of Embodiment 1

Figure 5A:
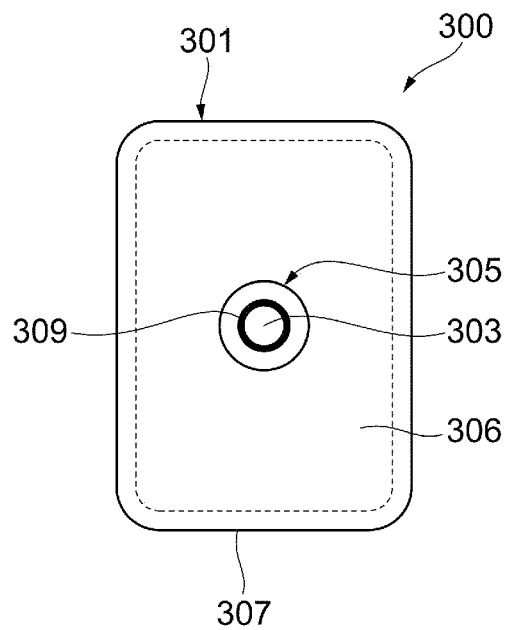
FIGS. 5(a)-5(c) illustrate Variation 3 of Embodiment 1 of an animal treatment apparatus according to the present invention.
Figure 5B:
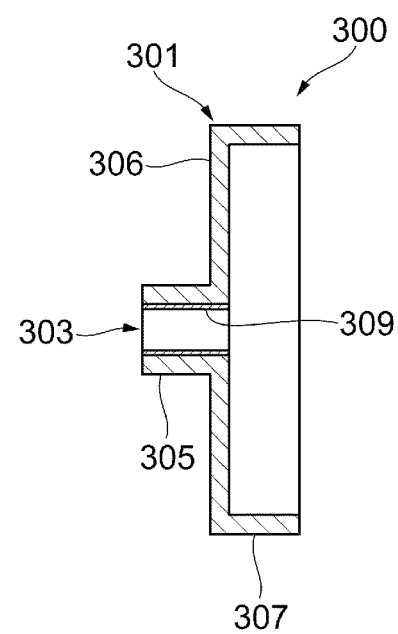
Figure 5C:
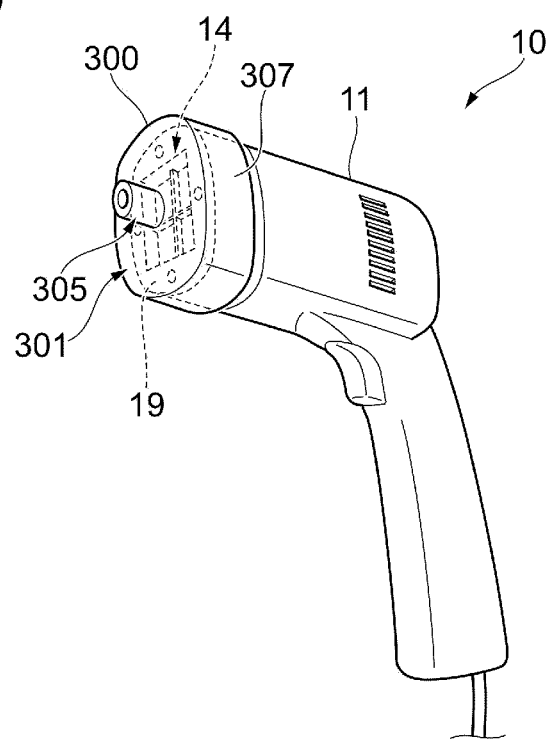

FIGS. 5(a)-5(c) illustrate another variation of the animal phototherapeutic apparatus 1.

The variation will be described below with reference to FIGS. 5(a)-5(c).

As previously described for the above-mentioned embodiment, the user presses the pressing surface 19 of the apparatus body 10 on the affected area or its vicinity to irradiate the area during the pressing. The user may irradiate the affected area, without contact of the apparatus body 10 with the animal. In other words, the animal phototherapeutic apparatus may be used to irradiate the affected area while the pressing surface 19 of the apparatus body 10 is spaced from the affected area or the like.

For example, in the case where the affected area to be irradiated is located in a depressed portion (hole) such as a nostril, an ear hole or a mouth, the user cannot irradiate the affected area while pressing the pressing surface 19 of the apparatus body 10 on the affected area. In this case, therefore, the user may be irradiated by accident.

Thus, a nozzle-equipped pressing member 300 as illustrated in FIGS. 5(a)-5(c) may be detachably attached to the apparatus body 10. When being attached to the opening 14 of the apparatus body 10, the nozzle-equipped pressing member 300 restricts the area through which the light emitted from the apparatus body 10 passes.

The nozzle-equipped pressing member 300 as illustrated comprises a covering 301, a through-hole 303 and a nozzle 305.

The covering 301 is a covering member to cover the opening 14 and the pressing surface 19. The covering 301 as illustrated comprises a base 306, which is a plate having a substantially rectangular shape in a planar view, and circumferential rib 307, which protrudes from the base 306 at its periphery. The base 306 has the through-hole 303 formed in the central region thereof. When the space defined by the base 306 and the circumferential rib 307 receive the forefront part of the apparatus body 10, the covering 301 can be disposed in place on the apparatus body 10 so that the through-hole 303 faces the opening 14.

The nozzle 305 is a substantially cylindrical member protruding from the base at the periphery of the through-hole 303. The nozzle 305 has on the inner wall, a reflecting layer 309, which may be composed of, for example, an aluminum film.

The apparatus body 10 including the above-described, nozzle-equipped pressing member 300 attached thereto can emit light through the through-hole 303 and the nozzle 305. In other words, the light emitted by the LED 21 exits the apparatus body 10 only through the front end of the nozzle 305. The lighting of LED 21 during the insertion of the front end of the nozzle 305 into the animal's ear or the like, inhibit the light from leaking outside the affected area. As the result, irradiation of the user with leaked light may be reduced.

The nozzle-equipped pressing member 300 may be formed in a shape corresponding to that of the affected area. For example, the outer diameter of the nozzle 305 may vary according to the type of the affected area. More specifically, if the affected area is in an ear hole, the nozzle 305 may be 20 mm in outer diameter, and if the affected area is in a nostril, the outer diameter of the nozzle 305 may be 7 mm in diameter.

The nozzle 305 as illustrated may include the reflecting layer 309 provided on the inner circumferential surface, so as to concentrate a larger amount of light on the affected area. It is not necessary that the reflecting layer 309 is provided on the inner circumferential surface of the nozzle 305. In other words, the nozzle 305 may not include the reflecting layer 309.

In the case in which the periphery of the mouth, or the rostrum, of the animal is irradiated, a cup- or truncated cone-shaped pressing member may be attached to the apparatus body 10. When being attached to the opening 14 of the apparatus body 10, the cup- or truncated cone-shaped pressing member can suppress the light emitted from the apparatus body 10 from leaking outside.

The cup- or truncated cone-shaped pressing member comprises a fitting member, which is fittable to the forefront part of the apparatus body 10, or an acceptor member, which is capable of accepting the forefront part, and a cup- or truncated cone-shaped reflector member. The reflector member includes on the inner lateral surface, a reflecting layer, which may be composed of, for example, an aluminum film.

The opening of the reflector member may be formed in a size and a shape corresponding to the shape of the area to be irradiated of the animal subject, or may be configured to be deformable according to the shape of the area to be irradiated. For example, the opening of the reflector member may be custom-made for individual subjects (with a 3D printer, for example) or may have an elastic member such as sponge, or a member like a contour gauge, attached thereto so that it can be closely contacted with the periphery of the area to be irradiated.

Other Variations of Embodiment 1

Although not illustrated, the animal phototherapeutic apparatus 1 may be configured to have the cable 50. In other words, the apparatus body 10 and the controller 30 are configured to be physically unconnected to each other. In this variation, the apparatus body 10 and the controller 30 may each comprise an adapter, wherein one of the adapters is detachably connectable to the other. More specifically, when one adaptor is connected to the other adaptor, it is possible to charge the apparatus body 10, to deliver control signals for the apparatus body 10, and others. In this configuration, the apparatus body 10 may further comprise a memory storage that stores the irradiation conditions set by the controller 30. In this case, the apparatus body 10 can operate according to the irradiation conditions stored in the memory storage, even when it is disconnected from the controller 30.

The present treatment apparatus 1 may comprise a mechanism emitting a sound or a smell during the lighting of any of the LEDs. The sound or smell may have an effect to calm and relax animals and therefore may reduce the animal's stress. The sound or smell may also allow the user to recognize LED lighting. It is preferable if the sound- or smell-emitting mechanism can emit one sound or smell selected from a plurality of sounds or smells so that the animal does not lose interest in the sound or smell emitted. The sound may be the sound of a music (such as a classical music), the voice of the owner, the sound of waves, the sound of a confectionery-packaging bag (crinkle sound) or the like.

In the sections "(Treatment protocol)" and "<Experiments>" described below, dogs' skin is irradiated with the light from the animal phototherapeutic apparatus 100, but the area to be irradiated is not limited to dogs' skin. Any animals other than dogs can also be irradiated. More specifically, the animal phototherapeutic apparatus 100 may be used for the treatment of a mammal (such as cat, horse, cow, pig or rabbit), a bird (such as chicken), a reptile (such as lizard), or the like. Animals to be treated are not particularly limited as far as they are non-human animals. It can be used to irradiate not only the skin but also any animal body parts, including mucosal tissues in an ear, oral cavity or the like, and parts exposed by incision. The method for irradiation of an animal body part is not particularly limited.

In the sections "(Treatment protocol)" and "<Experiments>" described below, the animal phototherapeutic apparatuses including the apparatus 1 emit the 310-nm light, 320-nm light, and 330-nm light, but the emitted lights are not limited to the said three lights. The emitted light may have a peak wavelength in the UV-B region (280-315 nm) and UV-A region (315-400 nm), preferably in the range of 280-340 nm.

More specifically, the emitted light may have one or more peak wavelengths in the range of 315-335 nm, and a relative intensity at wavelengths less than 315 nm of 30% or less. The relative intensity at wavelengths less than 315 nm is desired to be as low as possible so as to reduce the adverse effect on humans. Thus, the emitted light has one or more peak wavelengths in the range of 315-335 nm and a relative intensity at wavelengths less than 315 nm of preferably 15% or less, more preferably 5% or less, and still more preferably 0%.

The light having a relative intensity at wavelengths less than 315 nm of 30% or less can be obtained by lighting, for example, the LED emitting light with a peak wavelength at 315 nm and the LED emitting light with a peak wavelength at 326 nm, provided that the illuminances of the two LEDs are the same. In a similar way, the light having a relative intensity at wavelengths less than 315 nm of 15% or less can be obtained by lighting, for example, the LED emitting light with a peak wavelength at 320 nm and the LED emitting light with a peak wavelength at 326 nm. Analogously, the light having a relative intensity at wavelengths less than 315 nm of 5% or less can be obtained by lighting, for example, the LED emitting light with a peak wavelength at 326 nm. The light having a relative intensity at wavelengths less than 315 nm of 0% can be obtained by lighting, for example, the LED emitting light with a peak wavelength at 315 nm and the LED emitting light with a peak wavelength at 335 nm and passing the light through a cut-off filter absorbing or reflecting light at wavelengths less than 315 nm. The irradiation window 15, disposed in the path of the light emitted by the LED(s), may be used as a cut-off filter.

The light emitted may have one or more peak wavelengths in the range of 315-325 nm, for example, and a relative intensity at wavelengths less than 315 nm of 50% or less. It is preferable if the emitted light has one or more peak wavelengths in the range of 315-325 nm, and a relative intensity at wavelengths less than 315 nm of 20% or less, more preferably 5% or less, and still more preferably 0%.

The light having a relative intensity at wavelengths less than 315 nm of 50% or less can be obtained by lighting, for example, the LED emitting light with a peak wavelength at 315 nm. In a similar way, the light having a relative intensity at wavelengths less than 315 nm of 20% or less can be obtained by lighting, for example, the LED emitting light with a peak wavelength at 320 nm. Analogously, the light having a relative intensity at wavelengths less than 315 nm of 5% or less can be obtained by, for example, lighting the LED emitting light with a peak wavelength at 325 nm. The light having a relative intensity at wavelengths less than 315 nm of 0% can be obtained by lighting, for example, the LED emitting light with a peak wavelength at 320 nm and passing the light through a cut-off filter absorbing or reflecting light at wavelengths less than 315 nm.

The wavelength of light emitted from the animal phototherapeutic apparatus 1 for irradiation may be selected depending on the thickness of the skin in the area to be irradiated. For example, a shorter wavelength (the 310-nm light) may be selected for irradiation of a thicker skin, such as the skin of the nose or a paw pad, and a longer wavelength (the 320-nm light) may be selected for irradiation of a thinner skin, such as the skin of the back or abdomen. A still longer wavelength (the 330-nm light) may be selected for irradiation of a further thinner skin such as the skin of axilla.

It has been reported that skin thickening occurs in a skin lesion of, for example, canine atopic dermatitis (as referred to in Nimmo JS., et al., Vet. Pathol., 27, 1990). According to the responsiveness to phototherapy, the 320-nm light, 310-nm light, or the like may be selected appropriately. A combination of the 310-nm light with the 320-nm light or the 330-nm light may be simultaneously emitted so that the combined light has a relative intensity at wavelengths less than 315 nm of, for example, 50% or less. In this case, it is preferable if the 310-nm light is irradiated at a dose less than the minimum dose that causes erythema. For example, the 310-nm light at a dose of 300 $mJ/cm^2$ or less, 200 $mJ/cm^2$ or less, 100 $mJ/cm^2$ or less, or 50 $mJ/cm^2$ or less may be combined with the 320-nm light or the 330-nm light at a dose of 400 $mJ/cm^2$ or more, 600 $mJ/cm^2$ or more, 1000 $mJ/cm^2$ or more, or 1,500 $mJ/cm^2$ or less.

Emitted light having a peak wavelength in the range of 315-335 nm is not visible and therefore it is envisaged that the light having a peak wavelength in the range of 315-335 nm is emitted simultaneously with a visible light (in the range of 360-830 nm) so that light emission can be visually recognized. The visible light may be a blue, green or red light, which is easy to be visibly recognized by humans. This configuration can suppress the light source of the phototherapeutic apparatus form being left turned on, thereby ensuring the safety of the veterinarian.

The UI 31 of the controller 30 may be configured to comprise a display screen for selecting whether the skin area to be irradiated is thick or thin, and the screen is operated by the user to determine the wavelength of the light to be emitted. Alternatively, the UI 31 of the controller 30 may comprise a display screen for selecting which body part (nose, back, or the like) is to be irradiated, or the degree of skin thickening, and the screen is operated by the user to determine the wavelength of the light to be emitted.

In the foregoing description, LEDs such as LED 21 are used as the light sources. However, the light sources used are not particularly limited, and may also be light sources, such as UV lumps, other than LEDs. The use of LED, such as LED 21, makes it possible to easily control the illuminance of the emitted light.

In the embodiment, the present apparatus may not have two or more light sources whose emission wavelengths are different from each other or one another. For example, the apparatus may be configured to comprise a single light source and two or more cut-off filters transmitting different wavelengths of light from each other or one another. Accordingly, the user can switch the light to be emitted by selecting any one of the cut-off filters, through which the light is transmitted from the single light source. The apparatus 1 may have a configuration incapable of switching the wavelengths of the light to be emitted. In other words, the apparatus 1 may have a configuration capable of emitting only a single light.

It is to be noted that the animal phototherapeutic apparatus 1 is an example of the animal treatment apparatuses and phototherapeutic apparatuses. The LED board 23 is an example of the support member. The cut-off filter is an example of the suppressing member. The second LED 212 is an example of the light source. The third LED 213 is an example of another light source. The first LED 211 is an example of another light source. The LED driver board 29 is an example of the switch. The control board 33 is an example of the controller. The 310-nm light is an example of the first light. The 320-nm light is an example of the second light. The LED 21 is an example of the light-emitting unit.

Embodiment 2

FIGS. 6(a) and 6(b) and 7(a) and 7(b) are schematic diagrams of animal treatment apparatus 400 according to Embodiment 2.

The general configuration of the animal treatment apparatus 400 will be described below with reference to FIGS. 6(a) and 6(b) and 7(a) and 7(b).

The animal treatment apparatus 400 comprises: a platform member 440, on which a leg A1 (particularly a foot) of an animal is placed; light-emitting units 421, 422, 423, 424 emitting ultraviolet light to the irradiation area defined on the top surface 415 of the platform member; and a cover member 442 covering the platform member from above, the cover member having an opening or a cutout, through which the animal leg passes.

In the embodiment, the distance between the affected area and the light-emitting unit can be kept constant by holding the affected area to be irradiated on the platform member at the predefined position. As a result, the variation of the illuminance at the irradiated area can be controlled. Particularly where the light-emitting unit is provided below the platform member, the variation of the illuminance at the affected area (for example, the affected area in a sole or between pads) can be controlled, regardless of whether the animal is large or small.

The light-emitting units 421-424 are arranged in such a manner that they can irradiate the irradiation area defined on the top surface 415 of the platform member from above and/or below the platform member, and/or laterally, and/or behind (in relation to the opening or the cutout 444), preferably from above and/or below, more preferably from below, the platform member. More specifically, the light-emitting units face the bottom surface of the platform member, and/or positioned on the ceiling part 417 and/or one, two or three lateral surface parts 416 of the cover member 442.

Where the light-emitting unit 421 is provided below the platform member 440, at least a part of the platform member corresponding to the irradiation area is made of a material(s) that is/are transparent to the light emitted from the light-emitting unit. Such materials include UV transparent glasses such as silica glass, UV transparent resins such as acrylic resins, silicone resins and fluorine-based resins, and the like. The platform member may function as a protector member of the light-emitting face of the light-emitting unit.

The platform member 440 may include a guide (of a recess(es) or a protrusion(s), for example) to guide the limb (particularly, the foot) to an appropriate position in relation to the irradiation area. The guide may be formed of a recess(es), or protrusion(s), defining the irradiation area. If a lower cover member 446 is included, the lower part of the platform member and the light-emitting unit 421 may be covered by the lower cover member 446.

The driver unit is preferably positioned in the vicinity or proximity of the light-emitting unit, but it can be located at any appropriate position of the present treatment apparatus.

The controller can be located at any appropriate position of the present treatment apparatus. The UI may be provided on, for example, a top or outer lateral surface of the cover member. Alternatively, the controller can be located in a control unit, which is outside of an apparatus body configured to comprise the platform member 440, the light-emitting units 421-424, the cover member 442 and optionally the lower cover member 446, and the UI can be provided on a top surface and/or a lateral surface of the control unit. In this configuration, the apparatus body and the control unit are connected via a cable.

The size of the opening or cutoff 444 is not particularly limited so long as it is sufficient for one or two limbs of the animal subject to pass through. The opening or cutoff may be substantially rectangular, for example. In the case in which the opening is substantially rectangular, its lower side is preferably in or below the same horizontal plane as the top surface of the platform member.

Figure 6:
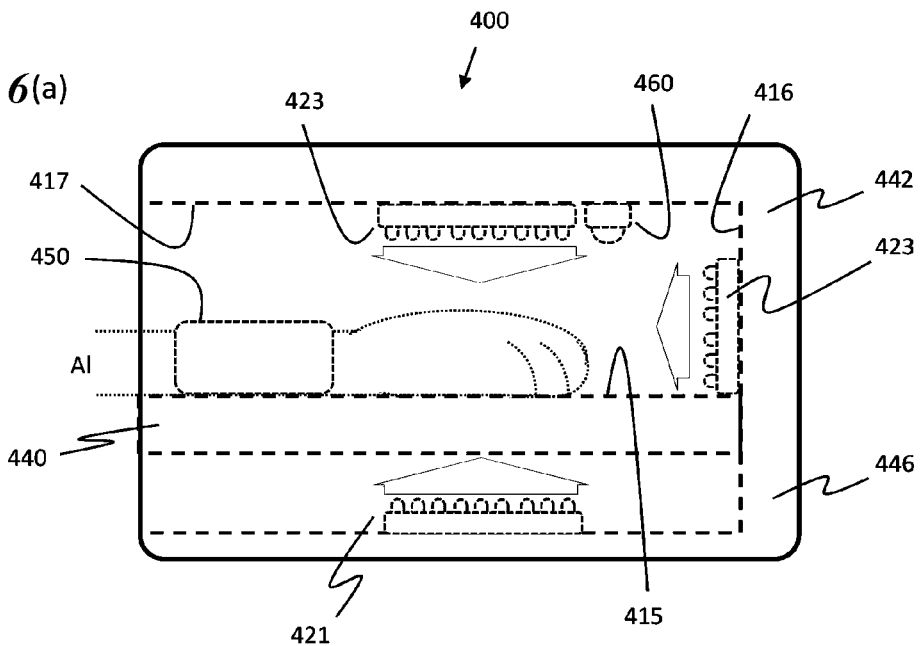
FIGS. 6(a) and 6(b) are schematic diagrams of Embodiment 2 of an animal treatment apparatus according to the present invention.
Figure 6:
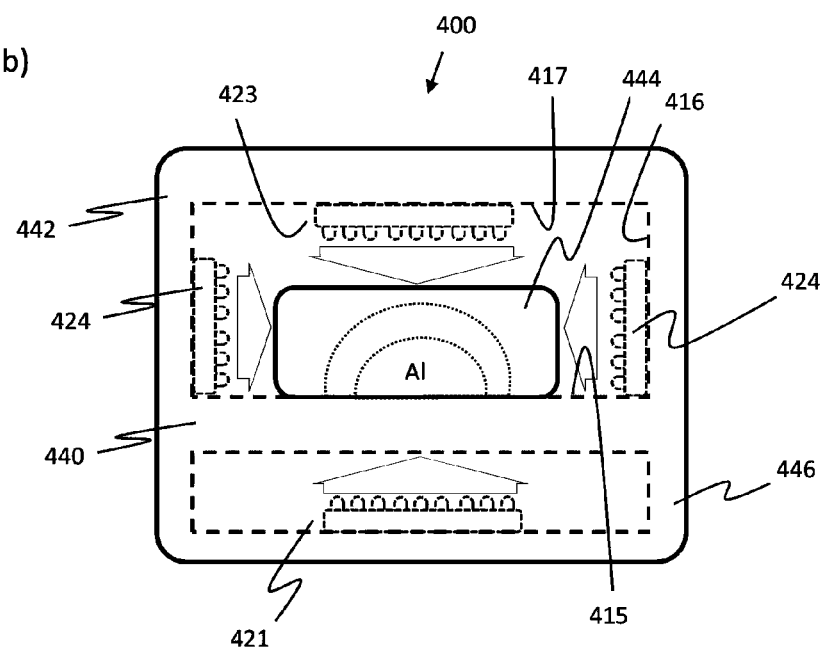

The treatment apparatus may comprise a holding mechanism 450 to hold the animal's limb disposed on the platform member by pressing it against the top surface 415 of the platform member. As illustrated in FIGS. 6(a) and 6(b), the holding mechanism 450 may be a belt. The belt may have a hook-and-loop fastener assembly to fix its two ends to each other. In this configuration, the platform member may have two slit, through which the belt passes or may be fixed to the platform member at one end. The belt may have an elastic member in its inside (the side to contact with the animal's limb).

Figure 7:
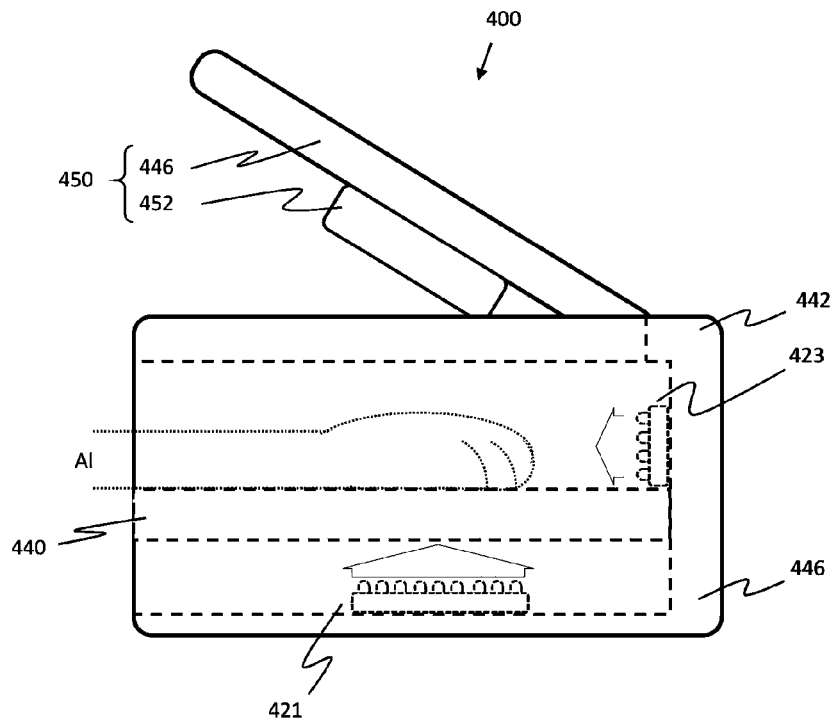
FIGS. 7(a) and 7(b) illustrate a variation of Embodiment 2 of an animal treatment apparatus according to the present invention.
Figure 7:
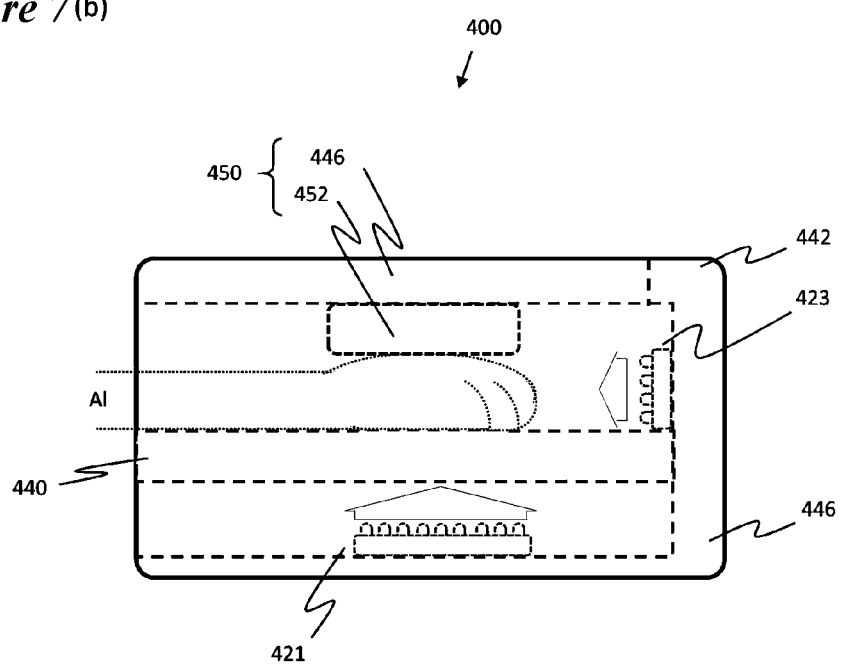

Alternatively, as shown in FIGS. 7(a) and 7(b), the holding mechanism 450 may be composed of a pressing member 452, which is moved in linkage with the operation opening and closing a lid 446, which is capable of open and close and is disposed in the cover member. The lid 446 is pushed down and presses the animal's limb onto the top surface 415 of the platform member when closing the lid 446, and lifted up and releases the animal's limb when opening the lid 446. The pressing member 452 may be an elastic member, more specifically a sponge (for example, rubber or synthetic resin foam). In this configuration, the animal's limb (the area to be irradiated) can be positioned in place on the top surface 415 of the platform member by positioning the animal's limb on the top surface in a state where the lid is up, followed by closing the lid. Therefore, the user can easily perform the positioning.

Alternatively, the holding mechanism may comprise an inflatable airbag and a limiting member to limit the upward inflation of the airbag with respect to the platform member. The airbag fed and inflated with air provides the down force as a result of the limitation of the inflation by the limiting member. The limiting member may be a band member fixed to the platform member, or a ceiling face of the cover member. A specific example of the holding mechanism is a cuff holder.

The treatment apparatus may comprise a sensor 460 that detects whether the animal's limb is positioned within the irradiation area on the top surface of the platform member. The sensor 460 is electrically connected to the controller. The controller is configured to allows the light-emitting unit to light on according to the input by the user or the like (for example, according to a switch that switches on and off the light-emitting unit, as described for Embodiment 1) when the sensor detects the presence of the animal's limb in the irradiation area. The controller is configured not to light on according to the input (for example, even if the switch is the on-position) when the sensor detects the absence of the animal's limb in the irradiation area. In the case in which the controller comprises a timer, it is configured to stop when the light-emitting unit lights off, to measure the time during which the light-emitting unit lights on (i.e., the time during which the treatment light is actually irradiated to the affected area). According to the configuration, the irradiation distance is constant and the irradiation time can also be measured more accurately, and therefore strict control of the irradiation dose can be achieved.

The treatment apparatus according to the embodiment is effectively used for the irradiation to the affected area in a limb, particularly in a digital(s) or between digitals (pads), of the animal.

Embodiment 3

In certain embodiments of the present animal treatment apparatus, the apparatus body is provided in the form of glove, for example, grooming glove. With the apparatus according to the embodiments, the animal is irradiated while being touched, so that the animal's stress may be reduced.

Figure 8A:
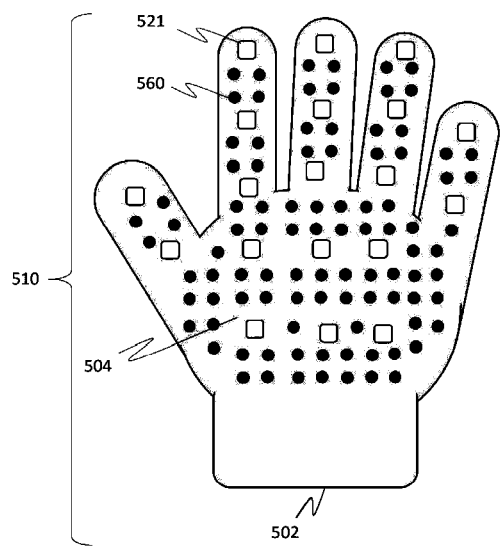
FIGS. 8(a) and 8(b) are schematic diagrams of Embodiment 3 of an animal treatment apparatus according to the present invention.
Figure 8B:
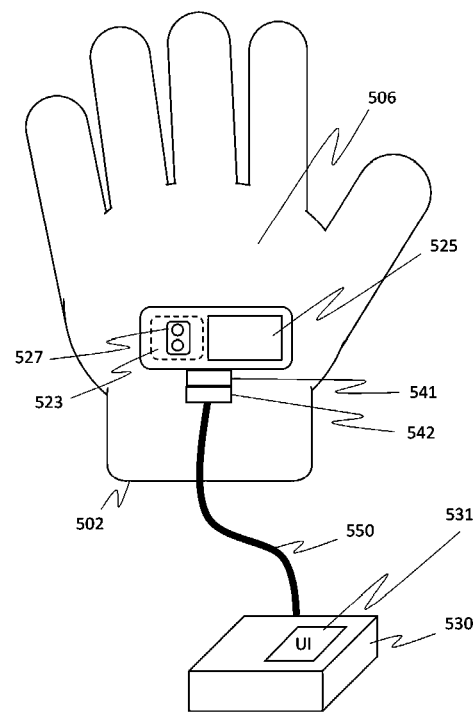

FIGS. 8(a) and 8(b) areschematic diagrams of another embodiment of the present animal treatment apparatus.

The general configuration of the embodiment of the present animal treatment apparatus will be described below with reference to FIGS. 8(a) and 8(b).

The apparatus body 510 according to the embodiment comprises a glove body 502 into which a human hand can be inserted, and at least one light-emitting unit 521 positioned on the palm-side outer surface 504 of the glove body, and a driver unit 523.

The light-emitting unit 521 may be arranged on the palm part and/or a finger part(s) of the glove. The driver unit 523 may be located on the back-side outer surface 506 of the glove body.

The apparatus body 510 may comprise a battery holder 525 on, for example, the back-side outer surface 506 of the glove body. According to this configuration, the apparatus body can receive power supply from a battery housed in the battery holder, and therefore does not need to be connected to an external power supply when used.

The controller may be or may not be provided on the apparatus body (glove body). In the configuration where the controller is not provided on the glove body, the driver unit 523 on the glove body can be electrically connected to the controller 530 provided outside the glove body via a pair of adaptors 541, 542. In this case, the adaptor 541 (one of the pair of the adaptors 541, 542) which is electrically connected to the driver unit 523 and as necessary a battery holder 525, is provided on the glove body 502, and the adaptor 542 (the other one of the pair of the adaptors 541, 542) is electrically connected to the controller 530 provided outside of the grove body via a cable 550.

When the controller 530 is electrically connected to the driver unit 523 (and optionally the battery holder 525) via the pair of adaptors 541, 542, information of the emission conditions for the light-emitting unit 521 is transmitted from the controller 530 and stored in a memory attached to the driver unit 523 and optionally the battery housed in the battery holder 525 is charged with power supplied from the controller 530.

On the back-side outer surface 506 of the glove body, a switch 527 may be provided, which switches on and off the light-emitting unit 521, and optionally the wavelengths of the light to be emitted.

On the palm-side outer surface 504 of the glove body, grooming or combing projections 560 may be provided. The projections 560 can be arranged on the palm part and/or a finger part(s) of the glove. With the glove having the projections, the irradiation can be carried out while the hairs are pushed aside, thereby achieving the efficient irradiation to the affected area (in particular, the affected area with hairs, such as the area affected with early stage atopic dermatitis).

The materials constituting the projections are not particularly limited so long as they are useful for grooming or combing, and may be resins (for example, UV transparent resins such as acrylic resins, silicone resins and fluorine-based resins). The shape and size of the projections can be appropriately determined according to the animal subject. The projections may have a comb-teeth-like shape.

Embodiment 4

In a certain embodiment of the present animal treatment apparatus, the apparatus body is provided in the form of brush or comb. With the apparatus according to the embodiment, the animal is irradiated while brushing or combing the hairs, so that the animal's stress may be reduced and efficient irradiation to the affected area with hairs (for example, the area affected with early stage atopic dermatitis) can be achieved.

Figure 9A:
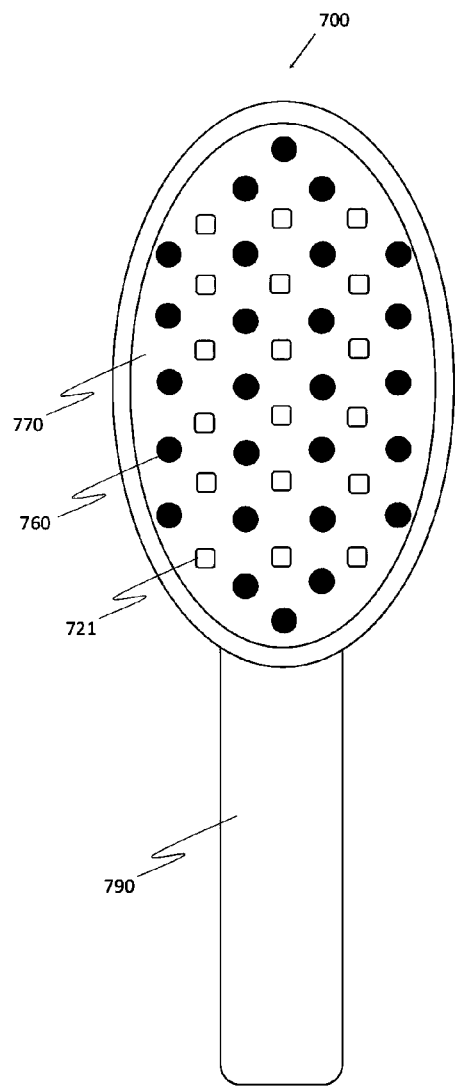
FIGS. 9(a) and 9(b) are schematic diagrams of Embodiment 4 of an animal treatment apparatus according to the present invention.
Figure 9B:
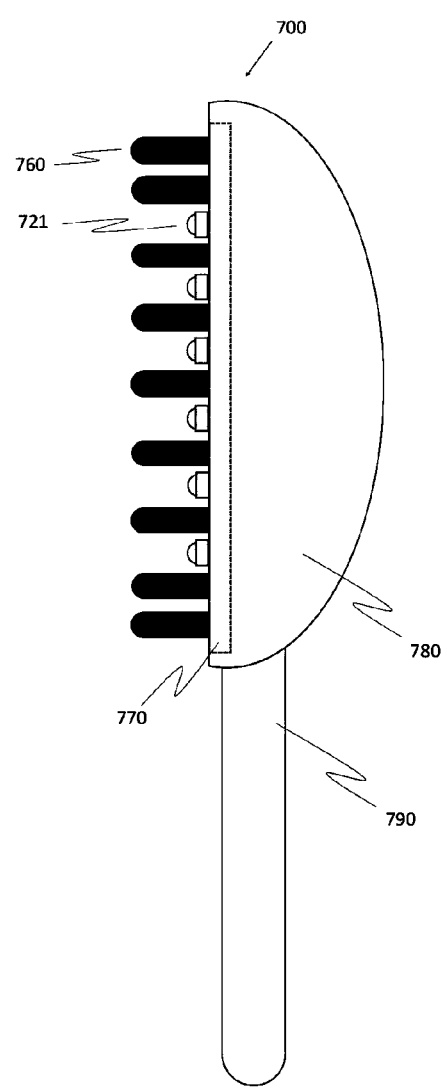

FIGS. 9(a) and 9(b) illustrate schematic diagrams of an animal treatment apparatus 700.

The general configuration of the animal treatment apparatus 700 according to the embodiments will be described below with reference to FIGS. 9(a) and 9(b).

The animal treatment apparatus 700 comprises a plurality of brush pins 760, a support 770 to support the brush pins, and a plurality of light-emitting units 721 arranged on the support.

In the apparatus 700, the light-emitting units 721 are arranged on the support 770 so that the lights emitted from the light-emitting units emit between the brush pins 760. For example, in the configuration wherein the brush pins are arranged in several lines, the light-emitting units can be provided between the lines. Alternatively, the brush pins are arranged around the light-emitting units.

The light-emitting units 721 may be provided in recesses in the support 770. In this configuration, the openings of the recesses may be covered by a member transmissive to the lights emitted from the light-emitting units (referred herein to simply as "transparent").

The shape and size of brush pins 760 can be appropriately determined according to the animal subject. Where the brush pins have a degree of rigidity, it is easy to keep the predetermined distance between the light-emitting units and the affected area to be treated. The brush pins 760 may be light guide members (of a UV transparent glass such as silica glass, UV transparent resins such as acrylic resin, silicone resin, fluorine-based resin, or the like, for example), meaning that they may serve as optical paths of the light emitted from the light emitting units. According to the configuration wherein the brush pins are light guide members, the lights emitted from the light-emitting units can irradiate to a wider area without being blocked by the brush pins. As a result, the variation of the illuminance at the area can be easily suppressed.

The animal treatment apparatus 700 may further comprise a back cover member 780 to cover the back surface (with no pins) of the support 770, and a gripper or handle 790. The back cover member may be integral with the gripper or handle.

The driver units may be provided as set with the respective light-emitting units or may all be positioned in an inner space defined by the support member and the back cover member. An optional battery holder can be provided in the said inner space or in an inner space of the gripper or handle.

The controller may be positioned on the outer surface of the back cover member. Alternatively, some components (driver circuits, for example) of the controller may be positioned in the inner space and another component(s) (UI, for example) may be positioned on the outer surface of the back cover member.

In the configuration in which the controller is not provided in the apparatus body in the form of brush, the driver unit in the apparatus body can be electrically connected to the controller provided outside the apparatus body via a pair of adaptors (see the description of Embodiment 3 and FIGS. 8(a) and 8(b).

In the apparatus body (for example, on an outer surface of the back cover member or the gripper or handle), a switch may be provided, which switches on and off the light-emitting units, and optionally the wavelengths of the light to be emitted.

Variation 1 of Embodiment 4

Figure 10A:
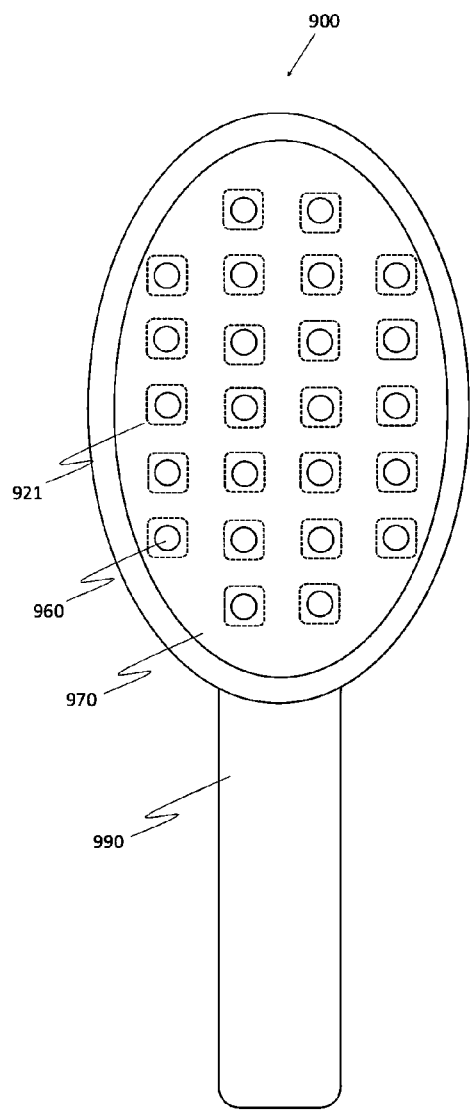
FIGS. 10(a) and 10(b) illustrate a variation of Embodiment 4 of an animal treatment apparatus according to the present invention.
Figure 10B:
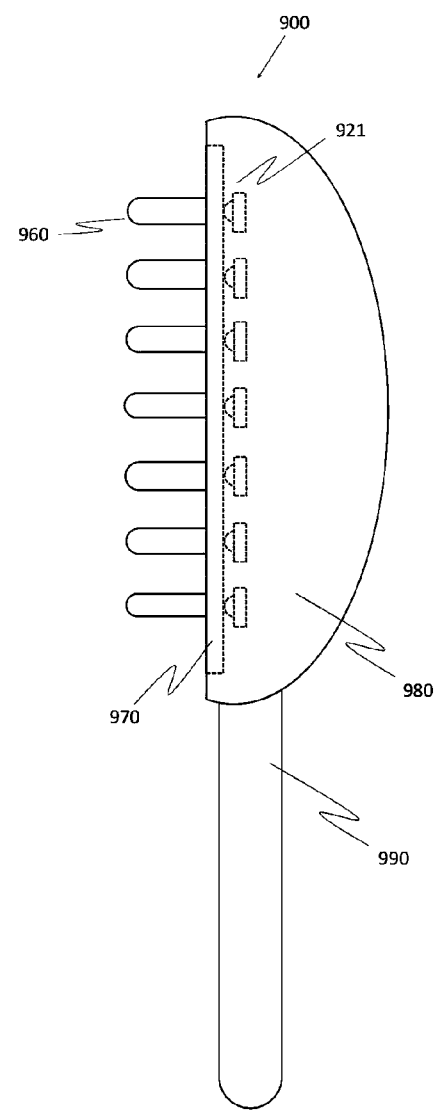

FIGS. 10(a) and 10(b) illustrate schematic diagrams of an animal treatment apparatus 900.

The general configuration of the apparatus 900 according to the embodiment will be described below with reference to FIGS. 10(a) and 10(b).

The animal treatment apparatus 900 comprises a plurality of brush pins 960, a support 970 to support the brush pins, and a plurality of light-emitting units 921 positioned on a side opposite to the brush pins with reference to the support member.

In FIGS. 10(a) and 10(b), the light-emitting units 921 are disposed to face the bases of the brush pins 960 through the support member 970, wherein the support member 970 is transparent and the brush pins 960 are light guide members.

The lights emitted from the light-emitting units 921 transmit the support member 970, then are guided through the brush pins 960, and exit to the brush pin side, so that the lights can irradiate to the animal. At least a portion of the lights emitted from the light-emitting units 921 may transmit the support member 970, and exit to the brush pin side.

Alternatively, the light-emitting units can be arranged to face a plurality of openings (or irradiation windows) of the support member so that the lights emitted from the light-emitting units can transmit the openings (or irradiation windows) and emit to the brush pin side.

Variation 2 of Embodiment 4

Figure 11A:
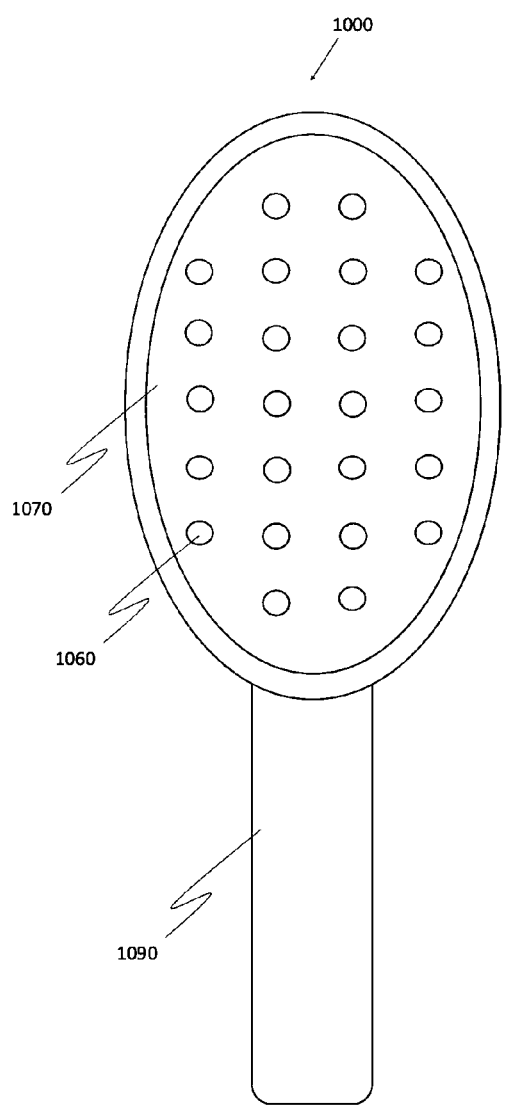
FIGS. 11(a) and 11(b) illustrate another variation of Embodiment 4 of an animal treatment apparatus according to the present invention.
Figure 11B:
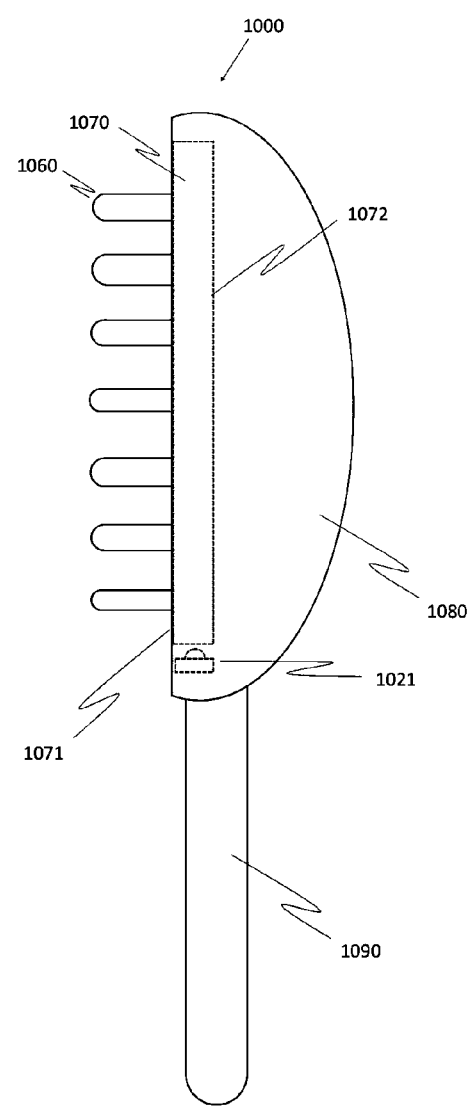

FIGS. 11(a) and 11(b) illustrate schematic diagrams of an animal treatment apparatus 1000.

The general configuration of the apparatus 1000 will be described below with reference to FIGS. 11(a) and 11(b).

The animal treatment apparatus 1000 comprises a plurality of brush pins 1060, a support 1070 that supports the brush pins and is light guide member, and one or more light-emitting units 1021 located at one or more ends of the support member.

In the apparatus 1000, the light-emitting units 721 are arranged on the support 770 so that the lights emitted from the light-emitting units enter the support member (light guide members) from its end(s) and exit from the surface 1071 on which the brush pins are located. On the surface 1072 on which no brush pins are provided, of the support member, a reflector may be provided. The brush pins may also be light guide members.

Other Variations of Embodiment 4

In the foregoing, brush-type apparatuses are described. In comb-type apparatuses, the light-emitting units can be disposed in a row(s) on one or both sides of a row of comb teeth.

Embodiment 5

Figure 12:
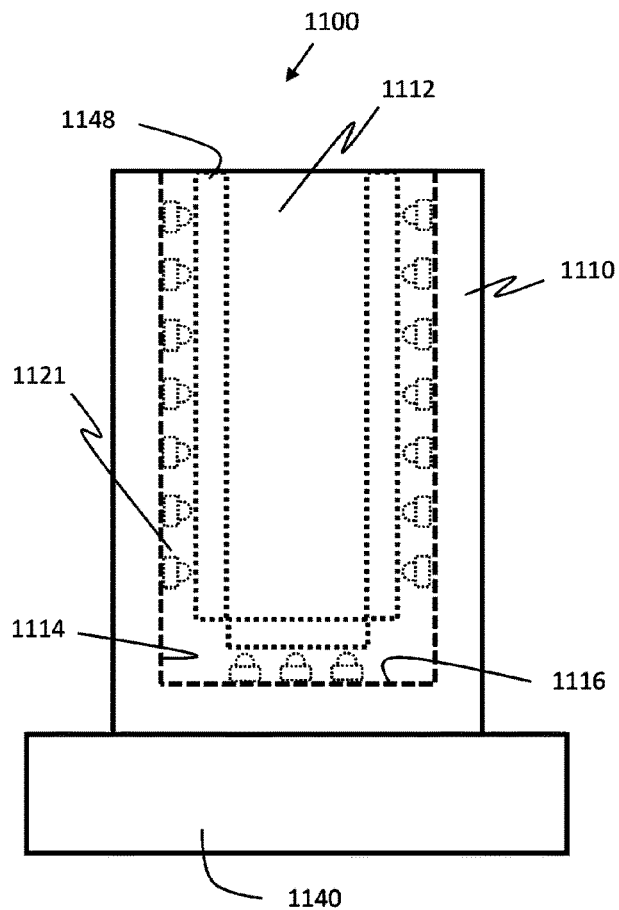
FIG. 12 is a schematic diagram of Embodiment 5 of an animal treatment apparatus according to the present invention.

FIG. 12 illustrates a schematic diagram of an animal treatment apparatus 1100 according to Embodiment 5.

The general configuration of the animal treatment apparatus 1100 will be described below with reference to FIG. 12.

The animal treatment apparatus 1100 comprises a hollow body 1110 to surround or accommodate the affected area of the animal's limb, and a light-emitting unit 1121 disposed to be able to irradiate inside the cavity 1112 of the hollow body.

The hollow body 1110 may have an inner and/or outer cross section(s) of circle or polygon (such as tetragon, pentagon, hexagon, octagon) in a plane perpendicular to the cavity axis. An example of the hollow body can be a cylinder. The hollow body may be configured to be composed of two half-split bodies which can be united into a cylindrical body. For example, the two half-split bodies are joined by a linking mechanism (for example, a hinge(s)) to each other, and locked in the joined state by a locking mechanism (such as a hook-and-loop fastener assembly, a draw latch).

The hollow body may or may not have a bottom. According to the embodiment wherein the hollow body does not have a bottom, the animal wearing the treatment apparatus is not restricted on movement, thereby reducing the animal's stress.

In FIG. 12, the hollow body 1110 is positioned so that the cavity axis is parallel to the vertical axis, but it can be positioned so that the cavity axis is inclined to the vertical axis.

The hollow body 1110 may be supported by a pedestal member 1140.

The light-emitting unit 1121 may be positioned to be able to irradiate to at least a part of the cavity 1112 of the hollow body 1110, so that the light-emitting unit can irradiate to the affected area of the animal's limb when surrounded by, or accommodated in, the cavity. The light-emitting unit 1121 can be provided on a lateral surface 1114 of the cavity 1112 of the hollow body. In the case in which the hollow body 1110 has a bottom as illustrated in FIG. 12 the light-emitting unit 1121 can be provided on the bottom surface 1116 of the cavity 1112 in addition to, instead of, the lateral surface 1114. A plurality of the light-emitting units may be arranged on lateral surfaces 1114 to surround the cavity 1112. For example, multiple (for example, 2-10, more specifically 2, 3, 4, 5, 6, 7 or 8) linear lighting units may be provided in parallel to the cavity axis.

On the cavity side of the light-emitting unit, a transparent protector member 1148 may be provided.

The driver unit is preferably positioned in the vicinity or proximity of the light-emitting unit 1121, but it can be located at any appropriate position of the treatment apparatus 1100.

The controller can be located at any appropriate position of the treatment apparatus 1100. The UI may be provided on, for example, an outer side surface of the hollow body 1110 or a top surface of the pedestal member 1140. Alternatively, the controller can be located in a control unit, which is outside of an apparatus body configured to comprise the hollow body 1110 to surround or accommodate the affected area of the animal's limb, and the light-emitting unit 1121 disposed to be able to irradiate to the cavity 1112 of the hollow body. The UI can be provided on a top surface and/or a lateral surface of the control unit. In this configuration, the control signal transmission and the power supply from the control unit to the apparatus body may be wired or wireless manner. In the case in which the apparatus body includes a battery holder, the electric power supplied to the apparatus body may be used to charge a battery housed in the battery holder.

An inflatable airbag may be provided in the cavity of the hollow body. Inflation of the airbag by being fed with air allows the animal's limb to be held in the cavity at a predefined position. As a result, the distance between the affected area and the light-emitting unit can be kept constant and therefore the variation of the illuminance at the area can be controlled. It is preferable if the airbag is formed of a transparent material(s). Such a transparent airbag does not interrupt the irradiation with the light emitted from the light-emitting unit to the affected area even when it is inflated. The airbag also serves as a protector member for the light-emitting unit.

The hollow body may comprise a shading cover to suppress the light emitted from the light-emitting unit from leaking through one or two openings of the hollow body to the outside. The shading cover is, for example, a lid having, in the center, a through hole through which the animal's limb passes. Where the hollow body is composed of two half-split bodies, the shading cover may be composed of two half-split bodies which can form, in the center, a through hole through which the animal's limb passes when joined and which are attached to the respective half-split bodies of the hollow body.

An inflatable airbag made of an opaque material(s) may be provided near an opening of the hollow's cavity. In the configuration, the airbag can serve as a holding mechanism to hold the animal's limb and a shading mechanism.

The treatment apparatus according to the embodiment is effective for irradiation of the affected area of the animal's limb. Particularly, the treatment apparatus wherein the apparatus body is a hollow body having a bottom and comprises a light-emitting unit on an inner bottom surface, is effective for irradiation of the affected area on a finger(s) or between fingers (pads).

Embodiment 6

The present animal treatment apparatus may comprise an apparatus body configured to be wearable. Such an apparatus may be, for example, of garment, belt, or boot type.

The apparatus body of garment type may have a vest-, pants- or sweater-type body, or the like.

The apparatus body of belt type is put on the animal by looping its belt body around the body or a limb of the animal. The belt member may have a locking mechanism at each end. Where the locking mechanism is a hook-and-loop fastener assembly for example, the apparatus body can be easily put on the animal by fastening the hook and loop strips.

The apparatus body of boot type may have a boot body capable of housing a foot of the animal.

Preferably, the material(s) for the garment, belt, or boot part is/are opaque to the light emitted from the light-emitting unit.

Figure 13:
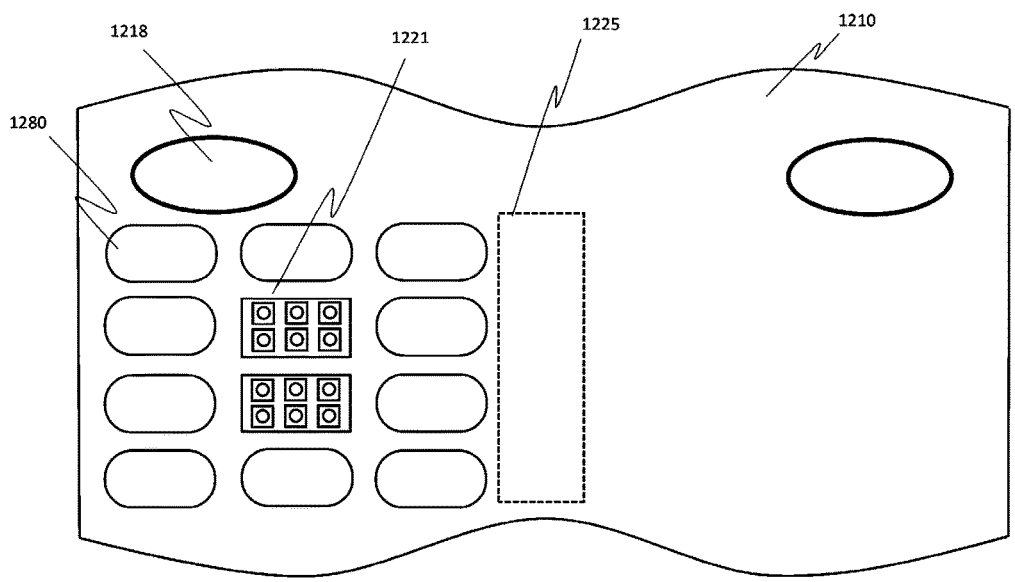
FIG. 13 is a schematic diagram of Embodiment 6 of an animal treatment apparatus according to the present invention.

FIG. 13 illustrates a schematic diagram of an animal treatment apparatus 1200 of garment type.

The general configuration of the animal treatment apparatus 1200 will be described below with reference to FIG. 13.

The animal treatment apparatus 1200 comprises a garment body 1210, and a light-emitting unit 1221 provided on the inner part (facing the animal when worn) of the garment body.

The light-emitting unit 1221 may be permanently fixed in a certain position, or attached by a detachable mechanism (such as hook-and-loop assembly) so that it can be positioned in any position corresponding to the affected area. In the figure, the light-emitting unit is positioned only on one of right and left bodies (on a right body), but may be positioned on both sides according to the affected area (to be irradiated).

At least one airbag 1280 may be provided around the light-emitting unit 1221. The airbag fed with air can serve to keep the distance constant between the affected area to be irradiated. According to the configuration, the variation of the illuminance at the irradiation area can be controlled. In the case in which the airbag is made of a material(s) opaque to the ultraviolet light emitted from the light-emitting unit, and is positioned to face an area not to be irradiated (skin area or the like other than the affected area), it also serves to reduce unnecessary irradiation to the area not to be irradiated. In the case in which the light-emitting unit is detachable, it is preferable if the airbag is also detachable.

The garment body 1210 may comprise a battery holder 1225. In the case in which the garment body 1210 includes a battery holder 1225, the battery holder 1225 is preferably positioned in the back part of the garment body on the outer side (not facing the animal when worn).

The garment body can have any shape wearable by the animal subject. The garment body may have forelimb holes 1218 to pass the forelimbs therethrough.

The driver unit is preferably positioned in the vicinity or proximity of the light-emitting unit, but it can be located at any appropriate position of the apparatus body. The driver unit may be or may not be included in the apparatus body.

The power supply to the apparatus body may be performed wired or wireless manner. In the case in which the apparatus body includes a battery holder, the electric power supplied to the apparatus body may be used for charging a battery housed in the battery holder.

The treatment apparatus according to the present embodiment, which comprises the apparatus body having a wearable structure, allows the animal subject to move freely (to be treated while walking, for example), thereby reducing the animal's stress, which is possibly caused by restriction or the like.

Embodiment 7

The animal treatment apparatus according to the present embodiment comprises an imaging unit that images an area including a lesion, an apparatus body comprising a light-emitting unit and a driver unit, and a controller, wherein the controller identifies the lesion based on image information received from the imaging unit, and controls the light-emitting unit and/or the driver unit to irradiate to the identified lesion.

The light-emitting unit may comprise optical a projector system (using a digital micromirror device).

The imaging unit may be, for example, a camera such as a digital camera. The camera may be positioned so that its field angle is identical to an irradiation field angle of the optical projector system of the light-emitting unit.

The controller may comprise an image processing circuit and process the images captured by the imaging unit to identify the lesion. The controller may determine the irradiation conditions based on the images of the lesion, using artificial intelligence or machine learning. In the configuration, the illuminance can be automatically adjusted according to the symptom of the lesion. The controller may be located in the apparatus body.

With the treatment apparatus according to the embodiment, ultraviolet light can be irradiated only to an (lesion) area(s) wherein erythema, alopecia, skin pigmentation or lichenification occurs. With the treatment apparatus, widespread skin lesions can be easily irradiated. The treatment apparatus, which also captures images during irradiation, can irradiate to the lesion following its movement even if the animal moves to some extent, thereby reducing unnecessary irradiation to normal areas.

Embodiment 8

The animal treatment apparatus according to the present embodiment comprises an animal accommodation unit that accommodates an animal, an apparatus body comprising a light-emitting unit and a driver unit, a swinging mechanism that horizontally and/or vertically swings the apparatus body, an affected-area-position identification unit that identifies the position of the affected area, and a controller, wherein the light-emitting unit is capable of emitting light having a peak wavelength in the range of 315-335 nm with high directivity and wherein the controller controls the swinging mechanism so as to direct the optical axis of the light-emitting unit to the position of the affected area, which position is identified by the affected-area-position identification unit, and the controller also controls the light-emitting unit and/or the driver unit to irradiate to the affected area.

The animal accommodation unit is not particularly limited as far as it can accommodate one or more animals therein. The animal holding unit may be, for example, a facility holding industrial animals (for example, cattle barn, pig barn, poultry house, or the like, or a space defined therein).

The affected-area-position identification unit may be, for example, a camera or a sensor. For example, the affected-area-position identification unit may identify the position of the affected area by detecting a luminescent agent, a magnetic agent, a microchip, a paint or the like, attached to, or embedded in, the affected area. Alternatively, the affected-area-position identification unit may recognize and identify the position of the affected area by image processing based on the previously stored images of the affected area.

The swinging mechanism can be a known swinging mechanism.

The controller may be positioned in the apparatus body.

The treatment apparatus according to the embodiment may further comprise a (second) sensor that detects the eyes' position and/or the movement of the animal. By detecting the eyes' position and/or the movement of the animal by the sensor, the animal's eyes are prevented from being irradiated with ultraviolet light.

The treatment apparatus according to the embodiment may be suitable for the treatment of large or fierce animals, which are hard to access, small animals, which move fast, and animals that are stressed by human contact. The treatment apparatus according to the embodiment can also be used for disinfection, sterilization, fungicide or viricide with ultraviolet light, and therefore serve also as a measure against infectious diseases such as avian influenza or classical swine fever.

Embodiment 9

The animal treatment apparatus according to a certain embodiment of the present invention comprises a light-emitting unit comprising LED light source, a driver unit comprising an LED driver circuit, a controller, a communication interface.

The treatment apparatus receives the irradiation conditions from the outside via the communication interface. For example, the irradiation conditions may be sent by a remote veterinarian via a public communication line such as a telephone line or internet line. The irradiation conditions can be determined by the veterinarian based on the images of the affected area, which images are taken and sent by the owner of the animal to the veterinarian.

The communication interface is an interface for communications with a communication terminal (such as a smartphone or a computer) accessible to a public communication line. The communication interface may be, for example, a wireless interface such as infrared interface, Bluetooth™, near-field communication interface or the like.

The controller is a CPU circuit, which may be, for example, a microcomputer board having a real-time clock. The controller receives the irradiation conditions sent from the communication terminal via the communication interface. The controller controls the light output from the light-emitting unit through the control of the driver unit according to the irradiation conditions received.

In the case in which the controller comprises a memory device, the irradiation conditions may be stored in the memory device. According to the configuration, the controller does not need to communicate with the communication terminal throughout use of the treatment apparatus.

The controller may comprise an interlocking mechanism to prevent lighting of the light source(s) of the light-emitting unit when the subject to be irradiated is not positioned in a predetermined position. The interlocking mechanism may be of contact type or contactless type. An example of contact-type interlocking mechanism uses a push switch. An example of contactless-type interlocking mechanism uses a photointerrupter or an infrared range finder.

The controller may comprise a D/A convertor (DAC) for setting an LED current, and optionally a timer for setting a cumulative amount of LED light and/or a counter for counting a total lighting time. The DAC for setting an LED current supplies current, which is needed for lighting the LED up, to the driver unit according to the irradiation conditions (especially the illuminance conditions). The timer is set at a time period for lighting LED for the treatment, according to the irradiation conditions (especially, dose conditions and illuminance conditions, or irradiation time conditions), and lights off the LED by stopping the LED current supply to the driver unit, when the LED lighting time reaches the predetermined time. The total counter measures the total time of the LED lighting to manage the lifetime of the LED.

The treatment apparatus may comprise a thermal sensor that senses the temperature of the irradiated area and/or the light emitting unit. In the configuration, the controller may have an A/D converter for reading the thermal sensor. The controller can forcibly stop the lighting of the light-emitting unit when the temperature of the irradiated area and/or the light-emitting unit measured by the thermal sensor is above the predefined temperature.

The controller may set the irradiation area by controlling an optical system provided in the light-emitting unit, according to the information regarding the distance from the irradiated area, which distance is measured by an infrared range finder.

The controller may transmit the information regarding an illuminance and an irradiation time, or a cumulative light amount, and/or a total lighting time, to the communication terminal via the communication interface. The information sent to the communication terminal may be displayed on a display device provided on the terminal, and/or transmitted to the veterinarian.

OTHER EMBODIMENTS

In an animal treatment apparatus according to an embodiment of the present invention, the apparatus body may be in a shape of mat. The mat shaped configuration of the apparatus body can reduce the animal's stress, which is possibly caused by restriction or the like.

In an animal treatment apparatus according to an embodiment of the present invention, the apparatus body may comprise a ring- or doughnut-shaped support, and a plurality of light-emitting units disposed on the support, wherein the light-emitting unit has cylindrical or comb-teeth-shaped light guide members. The apparatus according to the embodiment may be suitable for treating the affected area around the eye.

The cylindrical (e.g., pin-shaped) or comb-teeth-shaped light guide members serve as optical paths to guide the light emitted by the light sources or light source modules of the light emitting units, to the surface of the affected area. The size of the support may be, for example, 40 mm in outer diameter and 20 mm in inner diameter.

In an animal treatment apparatus according to an embodiment of the present invention, the apparatus body may be in the form of mouthpiece or toy, which is bitten or held in the mouth by the animal. In the embodiment, at least a part of the mouthpiece or toy may be formed of a light guide material(s), and the light emitted by the light source or light source module of the light emitting unit may be guided to the gingiva or the buccal cavity. Preferably, the mouthpiece or toy is formed of an elastic material(s). The apparatus according to the embodiment may be suitable for treating the affected area on the gingiva or in the oral mucosa.

An animal treatment apparatus according to an embodiment of the present invention may be configured to be incorporated into an endoscope. Such an endoscope may be a capsule endoscope. The apparatus according to the embodiment may be effective for treating mucosa diseases and disorders in, for example, the digestive system.

<Treatment Method>

A treatment method according to an embodiment of the present invention is a method for treating a non-human animal subject, the method comprising a step of irradiating one or more times, an affected area of the subject with light having a peak wavelength in the range of 315-335 nm.

The animals that can be treated by a treatment method according to embodiments of the present invention are not particularly limited as far as they are non-human animals, and are those animals that can be subjected to a veterinary treatment, including companion animals, pet animals, zoo animals, industrial animals (e.g., farm animals), and wild animals. The animals are, for example, mammals, birds and reptiles, preferably mammals and birds. Specific examples of the animals include dog, cat, monkey, chimpanzee, rabbit, squirrel, guinea pig, hamster, mouse, rat, cow, pig, horse, sheep, goat, chicken, pigeon, parakeet, parrot, myna, duck, dabbling duck, turkey, guinea fowl, goose, ostrich, and lizard.

As described below, an allergic reaction is suppressed in such an area of an animal that is irradiated with light having a peak wavelength in the range of 315-335 nm. Thus, the disease or disorder that can be treated by a treatment method according to embodiments of the present invention, is an allergic disease or disorder, such as allergodermia, allergic rhinitis or inflammatory bowel disease. The disease or disorder is preferably an allergodermia and more particularly atopic dermatitis, atopic-like dermatitis, a dermatitis associated with an adverse food reaction (food allergy) or the like.

In general, the expression level of MrgprX2 (Mas-related G-protein coupled receptor member X2) is decreased in the irradiated area. MrgprX2 is a target molecule of a factor promoting the degranulation response in mast cells (Tatemoto K et al., Biochem. Biophys. Res. Commun., 2006, 349(4): 1322-1328). The pseudo-allergic drug reactions are known to disappear in the mice lacking MrgprB2, corresponding to human MrgprX2 (McNeil B D et al., Nature, 2015, 519(7542): 237-241). The expression of MrgprX2 is upregulated in skin tissues from human subjects with severe chronic urticaria (Fujisawa D. et al., J. Allergy Clin. Immunol., 2014, 134(3): 622-633). Therefore, it is believed that the suppression of MrgprX2 expression can heal or relieve allergy symptoms. Thus, the disease or disorder that can be treated by a treatment method according to an embodiment of the present invention, may be a disease or disorder associated with MrgprX2 gene, and more specifically a disease or disorder (in particular, allergodermia) caused by enhanced expression of MrgprX2 gene.

It has been observed that in the irradiated area, the expression levels are increased for the genes for keratin and epidermal growth factors such as FBN2 and that the expression levels are changed for the genes involved in the differentiation or neogenesis of myofibroblasts or fibroblasts. Thus, a treatment method according to an embodiment of the present invention may be also effective in the treatment of skin wounds.

Furthermore, as described below, the irradiation with light having a peak wavelength in the range of 315-335 nm can alleviate a symptom of erythema, vitiligo, alopecia, lichenification, and epidermolysis. In this connection, it is known that medium wavelength ultraviolet light (UVB), such as narrow band UVB, can be effective in the treatment of atopic dermatitis, vitiligo, psoriasis, palmoplantar pustulosis, parapsoriasis, prurigo nodularis, alopecia, cutaneous T-cell lymphoma, and the like in humans. As described below, light having a peak wavelength in the range of 315-335 nm is as therapeutically effective in animals other than human as light having a peak wavelength at 310 nm. Therefore, it is believed that a treatment method according to an embodiment of the present invention is effective in the treatment of atopic dermatitis, vitiligo, psoriasis, palmoplantar pustulosis, parapsoriasis, prurigo nodularis, alopecia, and cutaneous T-cell lymphoma.

In addition, it is known that alleviation of a dermatitis symptom suppresses bacterial growth. Therefore, it is believed that the treatment of dermatitis with a treatment method according to an embodiment of the present invention can improve or restore the balance of the skin bacterial flora, meaning that the method is effective in the treatment of a disease or disorder, such as pyoderma, caused by the growth of bacteria, such as *Staphylococcus* and/or *Streptococcus*.

Furthermore, it is believed that the treatment of dermatitis with a treatment method according to an embodiment of the present invention may be effective in the treatment of dermatophytosis, *Malassezia* infection, and viral skin infections Thus, the disease or disorder that can be treated by a treatment method according to an embodiment of the present invention, is preferably selected from the group consisting of allergic dermatitis, cutaneous lymphoma, vitiligo, wound, alopecia, infectious diseases, skin abscess and pyoderma.

Moreover, it is expected that a treatment method according to an embodiment of the present invention may be effective in the treatment of mastocytoma, melanocyte tumor and tumor-like lesions, specifically melanocytoma-acanthoma, malignant melanoma, and melanocytic hyperplasia.

The affected area or the area to be irradiated may be located in any of the head (including nose, ears and rostrum), body and limbs of an animal subject. The area may be such an area that can be non-invasively irradiated or that can be irradiated only after an invasive procedure such as a surgical operation. The area may be located in skin or mucosa, for example.

Light at wavelengths less than 315 nm comprises light at wavelengths of 260 and 280 nm readily absorbed by DNAs and proteins, respectively. Therefore, it is concerned that irradiation of animals and humans with the light at wavelengths of 260 and 280 nm causes an adverse effect thereon. Thus, it is desirable that light at wavelengths less than 315 nm is not irradiated or is irradiated at as low irradiation dose as possible unless needed. Preferably, light having a peak wavelength in the range of 315-335 nm is irradiated in such a manner that the relative illuminance of light at wavelengths less than 315 nm is 50% or less. The relative illuminance of light at wavelengths less than 315 nm whose peak wavelength is in the range of 315-335 nm is more preferably 30% or less, more preferably 20% or less, more preferably 10% or less, more preferably 5% or less, and more preferably 2% or less.

The irradiation dose of the light having a peak wavelength in the range of 315-335 nm for irradiation of an animal is not particularly limited as far as it is an effective amount (a therapeutically effective amount) for healing the subject disease or disorder to be treated or alleviating a symptom thereof in the animal, and as far as the does not cause an adverse effect (such as skin sunburn) to the skin of the animal. For example, the lower limit of the irradiation dose may be 10 mJ/cm$^2$, 20 mJ/cm$^2$, 30 mJ/cm$^2$, 50 mJ/cm$^2$, 80 mJ/cm$^2$, 100 mJ/cm$^2$, 200 mJ/cm$^2$, or 300 mJ/cm$^2$, and the upper limit may be 2000 mJ/cm$^2$, 1500 mJ/cm$^2$, 1000 mJ/cm$^2$, 800 mJ/cm$^2$, 500 mJ/cm$^2$, or 400 mJ/cm$^2$. In the case in which the illuminance is less than 10 mJ/cm$^2$, neither of healing the disease or disorder or alleviating a symptom thereof may be achieved. In the case in which the irradiation dose is greater than 2000 mJ/cm$^2$, it is highly likely that an adverse effect is caused to the irradiated area. A specific dose can be determined appropriately by a veterinarian according to the conditions of the affected area and/or the general conditions of the animal.

The illuminance of the light is not particularly limited. In view of therapeutic efficiency and/or ease of illuminance control, the illuminance may be selected appropriately within the ranges of, for example, from 0.1-300 mW/cm$^2$, more particularly from 0.5-200 mW/cm$^2$, more particularly from 1-100 mW/cm$^2$, more particularly from 5-50 mW/cm$^2$, and more particularly from 5-20 mW/cm$^2$.

In the case in which the distance from the treatment apparatus to the irradiated area (irradiation distance) can be kept substantially constant, the irradiation dose can be estimated from the illuminance and the irradiation time (irradiation dose=illuminance×irradiation time). In this case, the irradiation dose can easily be managed. In the case in which the irradiation distance may vary, it is possible to manage the irradiation dose by use of an UV cumulative light quantity measurement film or sheet (for example, UV scale manufactured by FUJIFILM Corporation).

The light having a peak wavelength in the range of 315-335 nm may be irradiated as continuous light or intermittent light (such as pulsed light). The use of intermittent light can avoid or reduce a rise in temperature of the irradiated area (the irradiation area (the affected area) and its vicinity) and/or the light source emitting the light. Pulsed light may have a pulse width of, for example, 100 ms or less, more particularly 50 ms or less, more particularly 20 ms or less, more particularly 10 ms or less, and more particularly 5 ms or less. Pulsed light may have a duty ratio of, for example, 50% or less, more particularly 40% or less, more particularly 30% or less, more particularly 20% or less, more particularly 10% or less, and more particularly 5% or less.

The light having a peak wavelength in the range of 315-335 nm may be extracted by using an optic filter, from the light with a wide wavelength spectrum emitted by a light source such as a halogen or mercury lump. The light having a peak wavelength in the range of 315-335 nm may be emitted by a light emitting diode (LED) or laser diode (LD) as a light source. In view of energy efficiency and economic efficiency, use of LED or LD is preferable due to the energy concentration, low heat generation, low power consumption and long life. In addition, the irradiation dose and/or illuminance can be easily controlled or managed.

In view of energy efficiency and economic efficiency, preferably, the light with a peak wavelength in the range of 315-335 nm has a main peak wavelength in the range of 315-335 nm.

In a treatment method according to an embodiment of the present invention, the light having a peak wavelength in the range of 315-335 nm is irradiated one or more times. For better therapeutic effect, two or more times of irradiation are preferable. The upper limit of the times of irradiation is not limited, but may be, for example, 21 times, 20 times, 15 times, 14 times, 10 times, 7 times, 5 times, 4 times, or 3 times.

In the case in which the irradiation is carried out two or more times, the irradiation doses for the second and subsequent irradiation may be the same as, or different from, the irradiation dose for the last or previous irradiation. In the case in which the doses for the second and subsequent irradiation are different from the dose for the last or previous irradiation, the doses for the second and subsequent irradiation may be lower but preferably higher than for the last or previous irradiation. The higher irradiation doses may be, for example, 30-200 mJ/cm$^2$ higher, and more specifically 50-150 mJ/cm$^2$ higher, than the dose of the last or previous irradiation. Alternatively, the higher doses may be, for example, 5-50% higher, and more specifically 10-20% higher, than the dose of the last or previous irradiation. Irradiation with increasing doses can be expected to have a better therapeutic effect.

In the case in which the irradiation is carried out two or more times, the wavelengths of the light for the second and subsequent irradiation may be the same as, or different from, the wavelength of the light for the last or previous irradiation. In the case in which the wavelengths of the light for the second and subsequent irradiation are different from the wavelength of the light for the last or previous irradiation, the wavelengths of the light for the second and subsequent irradiation may be longer or preferably shorter than for the last or previous irradiation. The shorter wavelengths may be, for example, 1-20 nm shorter, and more specifically 5-10 nm shorter, than the wavelength of the last or previous irradiation. Irradiation with decreasing wavelengths can be expected to have a better therapeutic effect.

One or both of the wavelength and the dose of light irradiation may be changed each time of irradiation. In the case in which both are changed, the dose is preferably reduced.

In the case in which the irradiation is carried out two or more times, the irradiation interval can be determined appropriately by a veterinarian according to the conditions of the affected area and/or the general conditions of the animal subject. The irradiation interval may be, for example, from 1 time/day to 1 time/week.

The light having a peak wavelength in the range of 315-335 nm can be irradiated simultaneously with light having a peak wavelength in the range of 305-315 nm. In this case, it is preferable to adjust the respective illuminances of the lights so that in the mixed light, the relative illuminance of light at wavelengths less than 315 nm is, for example, 50% or less. The light having a peak wavelength in the range of 305-315 nm is preferably irradiated at an irradiation dose less than the minimum dose that causes erythema. For example, the irradiation with the light having a peak wavelength in the range of 305-315 nm at a dose of 300 mJ/cm$^2$ or less, 200 mJ/cm$^2$ or less, 100 mJ/cm$^2$ or less, or 50 mJ/cm$^2$ or less is combined with the irradiation with the light having a peak wavelength in the range of 315-335 nm at a dose of 400 mJ/cm$^2$ or more, 600 mJ/cm$^2$ or more, 1000 mJ/cm$^2$ or more, or 1500 mJ/cm$^2$ or more.

An embodiment of a treatment method according to the present invention comprises:
a first step of irradiating the skin of a non-human animal subject with light having a peak wavelength in the range of 315-335 nm at a predetermined irradiation dose; and
a second step of irradiating the skin with the light irradiated in the first step at another irradiation dose that is higher than the irradiation dose in the first step, or light having a shorter peak wavelength than the peak wavelength in the first step, one or more days after the irradiation in the first step.

In this embodiment, the predetermined irradiation dose in the first step can be determined appropriately by a veterinarian according to the conditions of the affected area and/or the general conditions of the animal subject. The predetermined irradiation dose may be, for example, 300 mJ/cm$^2$ or less, in particular, 10-300 mJ/cm$^2$, specifically 10 mJ/cm$^2$, 20 mJ/cm$^2$, 30 mJ/cm$^2$, 50 mJ/cm$^2$, 80 mJ/cm$^2$, 100 mJ/cm$^2$, 200 mJ/cm$^2$, or 300 mJ/cm$^2$. Alternatively, the predetermined irradiation dose can be determined on the basis of the minimal erythema dose as determined for the animal subject. In the latter case, the predetermined dose may be, for example, from 5%-60%, specifically 50%, 40%, 30%, 20%, or 10%, of the minimal erythema dose.

The another dose may be a dose at which the irradiated light does not cause sunburn to the skin and which is, for example, 30-200 mJ/cm$^2$ higher, and more specifically 50-150 mJ/cm² higher, or which is, for example, 5-50% higher, and more specifically 10-20% higher, than the predetermined dose.

In this embodiment, the light having a peak wavelength in the range of 315-335 nm in the first step may be light having a peak wavelength in the range of 325-335 nm, and the light having a peak wavelength in the range of 315-335 nm in the second step may be light having a peak wavelength in the range of 315-325 nm.

Another embodiment of a treatment method according to the present invention comprises the steps of:
 (a) irradiating a skin of a non-human animal subject one or more times with light having a peak wavelength in the range of 315-335 nm at a predetermined first dose;
 (b) irradiating a skin one or more times with the light having a peak wavelength at a second dose that is higher than the first dose; and
 (c) repeating the step (b) with the second dose increasing each repetition, in this order.

The method according to this embodiment may further comprise, subsequent to the step (c), the step of:
 (d) irradiating the skin one or more times with light having a peak wavelength in the range of 315-335 nm (second peak wavelength) shorter than the peak wavelength (first peak wavelength), at a predetermined third dose.

The method according to the embodiment may further comprise, subsequent to the step (d), the step of:
 (e) repeating step (d) with the third dose increasing each repetition.

The method according to the embodiment may further comprise, subsequent to the step (e), the step of:
 (f) irradiating the skin one or more times with light having a peak wavelength in the range of 305 to 315 nm (third peak wavelength) at a predetermined fourth dose.

The method according to the embodiment may further comprise, subsequent to the step (f), the step of:
 (g) repeating step (f) with the fourth dose increasing each repetition.

In the specific embodiments, the peak wavelength in step (a) (hereinafter also referred to as "first peak wavelength") is not particularly limited as far as it is in the range of 315-335 nm. For example (particularly if the method comprises step (d)), the first peak wavelength is on the longer side of the range in 315-335 nm, specifically in the range of 325-335 nm.

The first dose in step (a) is as described above for the predetermined dose in the first step.

The second dose in step (b) may be, for example, 30-200 mJ/cm² higher, and more specifically 50-150 mJ/cm² higher, or alternatively, for example, be 5%-50% higher, and more specifically 10%-20% higher, than the first dose. The second dose may be such a dose that does not cause sunburn to the skin.

In step (c), the light with the first peak wavelength is irradiated to the skin of the animal subject one or more times at a dose that increases every one or more irradiations.

In step (c), an increment in dose may be, for example, 30-200 mJ/cm², and more specifically 50-150 mJ/cm². Alternatively, the increment in dose may be, for example, 5%-50%, and more specifically 10%-20%, of the first dose.

The upper limit of the increasing dose in step (c) is a dose at which the light having the first peak wavelength does not cause sunburn to the skin of the animal subject. This means that step (c) can be repeated until when the dose reaches the upper limit.

The second peak wavelength in step (d) is not particularly limited as far as it is in the range of 315-335 nm and shorter than the first peak wavelength. The second peak wavelength may be, for example, 5 nm shorter, 10 nm shorter, 15 nm shorter, or 20 nm shorter, than the first peak wavelength. For example, in the case in which the first peak wavelength is in the range of 325-335 nm, the second peak wavelength may be in the range of 315-325 nm.

The third dose in step (d) is as described above for the predetermined dose in the first step. The third dose may equal to the first dose.

In step (e), the light having the second peak wavelength is irradiated to the skin of the animal subject one or more times at a dose that increases every one or more irradiations.

In step (e), an increment in dose may be, for example, 30-200 mJ/cm², and more specifically 50-150 mJ/cm². Alternatively, the increment in dose may be, for example, 5%-50%, and more specifically 10%-20%, of the third dose.

The upper limit of the increasing dose in step (e) is a dose at which the light having the second peak wavelength does not cause sunburn to the skin of the subject. This means that step (e) can be repeated until when the dose reaches the upper limit.

The third peak wavelength in step (f) is not particularly limited as far as it is in the range of 305 to 315 nm.

The fourth dose in step (f) is as described above for the predetermined dose in the first step. The fourth dose may equal to the first dose.

In step (g), the light having the third peak wavelength is irradiated to the skin of the animal subject one or more times at a dose that increases every one or more irradiations.

In step (g), an increment in dose may be, for example, 30-200 mJ/cm², and more specifically 50-150 mJ/cm². Alternatively, the increment in dose may be, for example, 5%-50%, and more specifically 10%-20%, of the fourth dose.

The upper limit of the increasing dose in step (g) is a dose at which the light having the third peak wavelength does not cause sunburn to the skin of the subject. This means that step (g) can be repeated until when the dose reaches the upper limit.

The number of irradiations in each of the steps can be determined appropriately by a veterinarian according to the conditions of the affected area and/or the general conditions of the animal subject, and may be, for example, from 1-14 times. The numbers of irradiations may be the same in all the steps, or different from each other or one another.

The irradiation interval can be determined appropriately by a veterinarian according to the conditions of the affected area and/or the general conditions of the animal subject and may be, for example, 24 hours (or 1 day) or more, and more specifically from 1-7 days. The irradiation interval may be constant during the treatment, or different in each step.

A treatment method according to embodiments of the present invention can be carried out with an apparatus according to the embodiments of the present invention as described above.

(Treatment Protocol)

Figure 14:
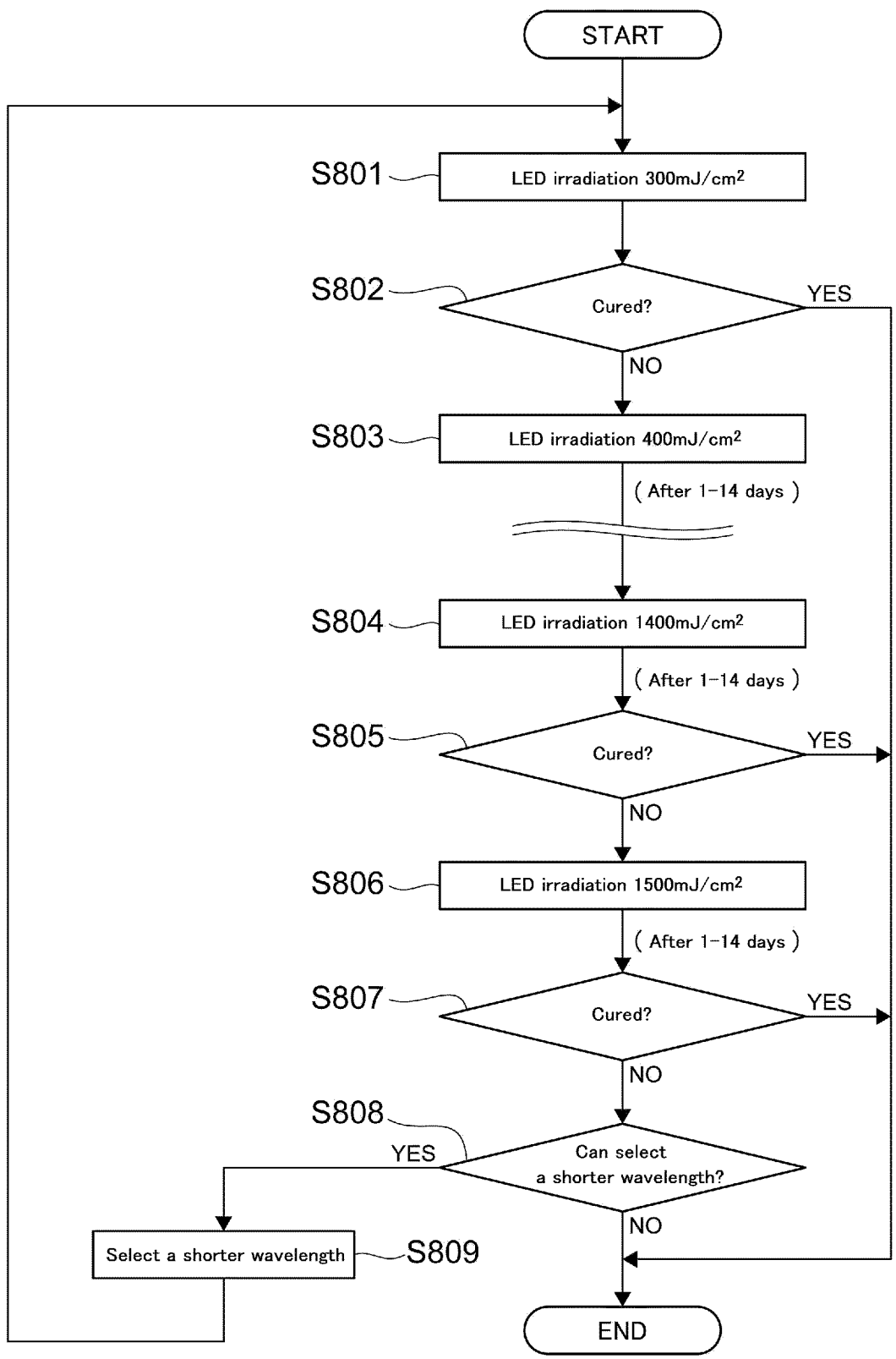
FIG. 14 illustrates a flowchart of the protocol for a treatment method according to the present invention.

FIG. 14 illustrates a flowchart of a specific treatment protocol used for a treatment method according to an embodiment of the present invention.

The protocol for the treatment of an animal subject with the animal phototherapeutic apparatus 1 will be described below with reference to FIG. 14. The protocol illustrated in FIG. 14 can be summarized as follows: the irradiation of an affected area, followed by judgment of whether the treatment is effective or not after a lapse of a prescribed period from the irradiation; and if unhealed, re-irradiation of the affected area at a higher dose. In the protocol as illustrated in FIG. 14, the affected area is treated with repeated irradiation of the 330-nm light at increasing doses, and if unhealed, then it is treated with repeated irradiation of the 320-nm light (or the 310-nm light) being as a shorter wavelength light, at increasing doses.

The treatment protocol will be specifically described below. To the affected area, the 330-nm light is irradiated at a dose of 300 mJ/cm² (S801). The dose of 300 mJ/cm² can be realized by the irradiation at an illuminance of 6.5 mW/cm² for 46 seconds, for example.

After a lapse of a prescribed period (1-14 days) from the irradiation, it is judged (or diagnosed) whether the disease or disorder has been healed or not (S802). If healed ("YES" in step S802), the treatment is completed and therefore the treatment protocol is terminated. If not ("NO" in step S802), the affected area is irradiated at a higher dose of 400 mJ/cm² (S803), that is 100 mJ/cm² higher than before increment (S801).

As briefly description, thereafter, if the disease or disorder is judged as unhealed, irradiation of the affected area is repeated while the dose is incremented by 100 mJ/cm². After the affected area is irradiated at a dose of 1,400 mJ/cm² (S804), it is judged whether the disease or disorder has been healed or not after the irradiation (S805). If healed ("YES" in step S805), the treatment is completed and therefore the treatment protocol is terminated. If not ("NO" in step S805), the affected area is irradiated at the maximum dose of 1,500 mJ/cm² (S806) and it is judged whether the disease has been healed or not after the irradiation (S807). If healed ("YES" in step S807), the treatment is completed and therefore the treatment protocol is terminated.

If not ("NO" in step S807), it is checked whether light at a shorter wavelength(s) can be emitted from the apparatus (S808). If light at a shorter wavelength(s) can be emitted ("YES" in step S808), the apparatus is set for emitting light at the shorter wavelength(s) (S809). Because, in the present case, the apparatus used is capable of switching from the 330-nm light to the 320-nm light, it is set for emitting the 320-nm light, which has a shorter peak wavelength (S809), and the 320-nm light is irradiated to the affected area with at a dose of 300 mJ/cm² (S801).

Subsequently, the steps S802 to S805 are repeated with the 320-nm light. Then, the 320-nm light is irradiated to the affected area at an incremented dose of 1,500 mJ/cm² (S806), and it is judged whether the disease or disorder has been healed or not after the irradiation (S807). If not healed ("NO" in step S807), it is checked whether light at a further shorter wavelength(s) can be emitted from the apparatus (S808). If light at a further shorter wavelength(s) can be emitted ("YES" in step S808), the apparatus is set for emitting light at the further shorter wavelength(s) (S809). In the present case, the apparatus is switched for emitting the 310-nm light from the setting for emitting 320-nm light, and then 310-nm light is then irradiated to the affected area at a dose of 300 mJ/cm² (S801).

Subsequently, the steps S802 to S805 are repeated with the 310-nm light. Then, the 310-nm light is irradiated to the affected area at an incremented dose of 1,500 mJ/cm² (S806), and it is judged whether the disease or disorder has been healed or not after the irradiation (S807). If not healed ("NO" in step S807), it is checked whether light at a still further shorter wavelength(s) can be emitted from the apparatus (S808). In the present case, animal phototherapeutic apparatus 1 cannot emit light having a peak wavelength shorter than 310 nm. Therefore, it is judged that light at a still further shorter wavelength(s) cannot be emitted ("NO" in step S808), therefore the treatment is ceased and the protocol is terminated.

It is known that ultraviolet light at wavelengths of 320 nm or more generally has less adverse effect on humans than light at wavelengths less than 320 nm, according to guidelines for treatments of humans with UV-B irradiation. Among the 310-nm light, the 320-nm light, and the 330-nm light that can be emitted from the animal phototherapeutic apparatus 1, the 320-nm light and the 330-nm light may have less effect on humans, or users of the apparatus 1. Accordingly, in the treatment protocol as described above, the affected area is first treated with the 330-nm light, which has the least adverse effect on users and is effective in the treatment of non-human animal subjects. If the therapeutic effect is poor, then the affected area is treated with the 320-nm light, which has the second least adverse effect on users and is effective in treating the animal subjects. If the therapeutic effect is still poor, then the affected area is treated with the 310-nm light. The treatment beginning with the 330-nm light may reduce DNA damage compared to that with the light used in the treatment of humans with UV-B irradiation, and is therefore safer for animal subjects and users.

The animal subject, such as a dog, to be treated with the apparatus 1 is often held and restrained during irradiation by a healer or veterinarian who is a user of the apparatus. In this situation, if the animal subject suddenly moves or wriggles during the irradiation, the user's arm, face or the like may be irradiated. In order to reduce the effect of irradiation on the user even in such a case, a longer wavelength light is preferentially used in the treatment protocol as described.

Although not described above, in the step of judging whether the disease has been healed or not (S802, for example) in the treatment protocol, it is also judged whether an adverse event, such as erythema, has occurred or not. This means that in the treatment protocol, the irradiation doses are increased to the extent that irradiation doses do not cause any adverse event, such as erythema.

If an adverse event is found, then the following protocol can be applied.

If the adverse event found is faint erythema, then the affected area is irradiated at the same dose as in the last or previous irradiation, meaning that the irradiation per se is continued while the dose is not increased.

If the adverse event found is clearly-marginated erythema, then the affected area is not irradiated on that day but is irradiated at the same dose as in the last or previous irradiation after a lapse of the prescribed period (1-14 days).

If the adverse event found is erythema with pain, edematous erythema or blisters, then the treatment protocol is discontinued until the symptom subsides (or is improved). After improvement of the symptom, the treatment protocol is re-started with a dose that is reduced by half of that for the last or previous irradiation.

The treatment protocol is terminated finally in the above description of FIG. 14, but the procedure is not limited thereto. For example, the treatment protocol may not be intended to cure the disease but may be implemented for not aggravating a symptom(s). In this case, irradiation is continuously repeated at an interval of 7-14 days with monitoring the symptom(s).

An increment in dose is 100 mJ/cm² in the above description of the treatment protocol illustrated in FIG. 14, but is not limited thereto as far as the dose is increased in a stepwise manner. For example, the dose may be incremented by 300 mJ/cm². An increment each time may not be constant.

In the above description of the treatment protocol illustrated in FIG. 14, after the light is switched from the 330-nm light to the 320-nm light (in step S809), the irradiation with the 320-nm light starts at a dose of 300 mJ/cm² (in step S801). However, the procedure is not limited thereto. For example, if the irradiation with the 330-nm light at the maximum dose of 1,500 mJ/cm² has no or little therapeutic effect, irradiation with the 320-nm light may start at a higher dose than 300 mJ/cm², such as 1,000 mJ/cm². In this case, the treatment period may be shorted.

Unlike the above description, the affected area is irradiated with the 330-nm light at a prescribed dose (such as 1000 mJ/cm²) and if no therapeutic effect is observed after a lapse of a prescribed period (1-14 days) from the irradiation, then the affected area may be irradiated with a shorter wavelength light (such as the 320-nm light) at a prescribed dose (such as 1000 mJ/cm²).

In the above treatment protocol, the step S801 of irradiation at a dose of 300 mJ/cm² is an example of the first step, and the step S803 of irradiation at a dose of 400 mJ/cm² is an example of the second step. The treatment protocol describes an example of non-human animal treatment method.

In a treatment method (for example, the above-described treatment protocol) according to an embodiment of the present invention, the light having a peak wavelength in the range of 315-335 nm may be irradiated to the affected area after using a photosensitizing agent such as psoralen used in PUVA therapy, more specifically, after the photosensitizing agent is taken through oral administration, injection, or application on the animal. A treatment method according to an embodiment of the present invention may be combined with the treatment with a steroid, a Janus kinase inhibitor and/or cyclosporine in the case in which the subject disease to be treated is an allergic disease or an immune system disease, or combined with the treatment with a molecular targeted drug (such as Palladia®; ZOETIS) in the case in which the subject disease is mast cell tumor or lymphoma.

Experiments

FIG. 15 is a table showing the results of minimal erythema dose tests.

Figure 16A:
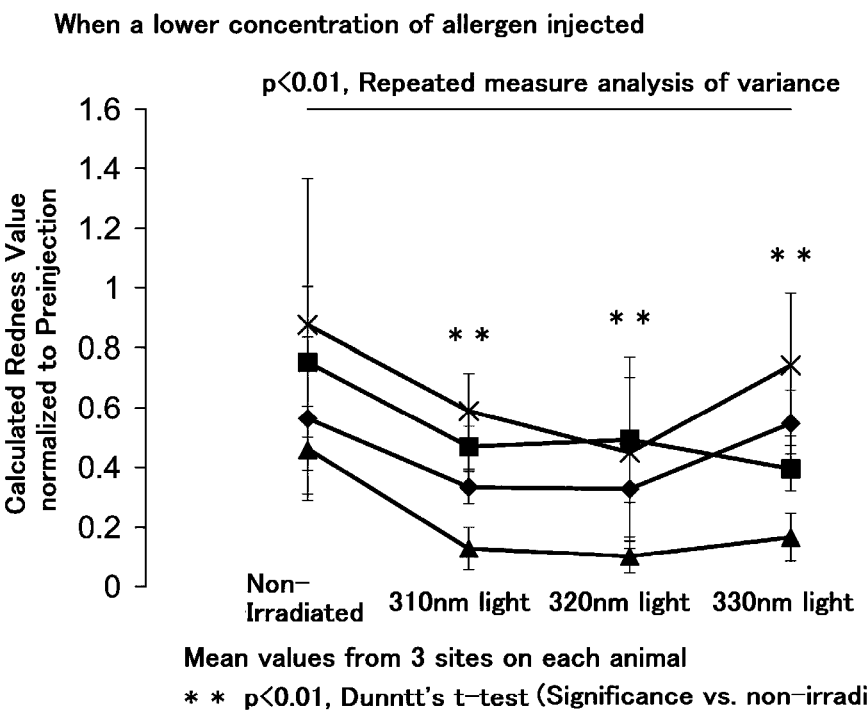
FIGS. 16(a) and 16(b) are graphs showing the results of allergic reaction inhibition tests.
Figure 16B:
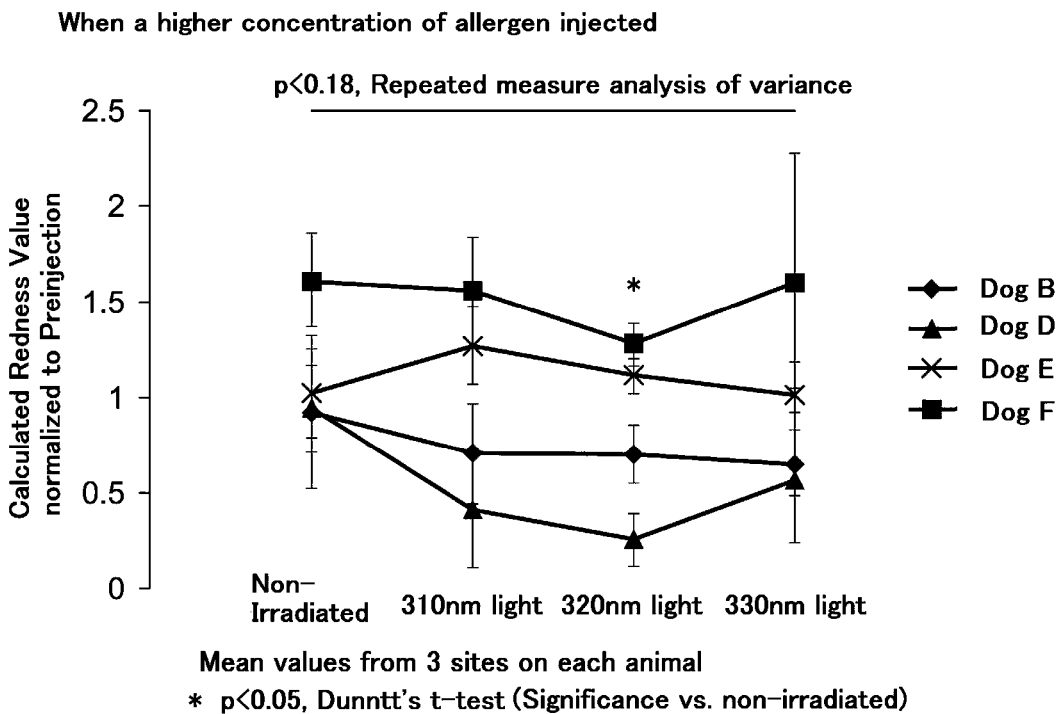

FIGS. 16(a) and 16(b) are graphs showing the results of allergic reaction inhibition tests.

FIG. 17 is a table showing the results of allergic reaction inhibition tests.

With reference to FIG. 15, FIGS. 16(a) and 16(b), and FIG. 17, a treatment method according to an embodiment of the present invention will be described below. More specifically, as the treatment method of an embodiment of the present invention, the minimal erythema dose test results and the allergic reaction inhibition test results will be described, which results were obtained in the experiments with the animal phototherapeutic apparatus 1.

(Minimal Erythema Dose Tests)

The results of minimal erythema dose tests will be described with reference to FIGS. 2 and 15. The minimal erythema dose is the minimal dose, at which ultraviolet irradiation of a skin will produce an acute symptom of the skin. In this example, the acute symptom is sunburn. Sunburn results primarily from DNA damage and is skin redness caused by engorgement, an inflammatory reaction, of capillaries. It is known that sunburn can increase the risk of skin cancer.

In the tests, the results of which are shown in FIG. 15, the hair on the back of each dog was shaved so that the skin was partially exposed. Light at different wavelengths was irradiated to the exposed skin at different doses and the reaction of the skin was observed. More specifically, the light emitted by the first LED 211, that is the 310-nm light, was irradiated to a total of 5 dogs: dog A to dog E. In each of the dogs A-E, 4 areas to be irradiated were established and then irradiated at respective doses of 200, 400, 800 and 1,500 mJ/cm². The light emitted by the second LED 212, that is the 320-nm light, was also irradiated to the two dogs D and E. In each of the dogs D and E, 4 areas to be irradiated were established and then irradiated at respective doses of 200, 400, 800 and 1,500 mJ/cm².

After irradiation under the conditions mentioned above, the irradiated areas were checked on whether sunburn occurred or not. The minimal dose producing sunburn among the 4 irradiated areas of each of the dogs was considered as the minimal erythema dose for each of the dogs. Sunburn was detected by imaging the skin areas before and 24 hours after irradiation and calculating the redness on the images.

As seen from FIG. 15, the minimal erythema doses for the 310-nm light were between 400 and 1,500 mJ/cm² with a large individual differences, while the 320-nm light did not cause detectable erythema even at a dose of 1,500 mJ/cm², confirming that the 320-nm light causes less sunburn than the 310-nm light. Thus, UV irradiation of skin with the 320-nm light has less adverse effect than with the 310-nm light, meaning that the 320-nm light is safer for dogs than the 310-nm light. The 320-nm light may cause less risk of skin cancer, because no detectable erythema was found in the areas exposed to the 320-nm light even at a dose of 1,500 mJ/cm².

In the minimal erythema doses tests described above, the minimal erythema doses were determined to be 400 mJ/cm² or more for both of the 310-nm light and the 320-nm light. In the allergic reaction inhibition tests described below, therefore, irradiation was carried out at a dose of less than 400 mJ/cm², specifically of 300 mJ/cm², so as to reduce causing sunburn. The dose used in the allergic reaction inhibition tests was 300 mJ/cm², however, the dose may be less than 300 mJ/cm², in other words, 300 mJ/cm² or less.

Allergic Reaction Inhibition Tests

The results of allergic reaction inhibition tests will be described with reference to FIGS. 2, 16(a), 16(b), and 17.

In the test, the results of which are shown in FIGS. 16(a), 16(b), and 17, light at different wavelengths was irradiated to the skin of the back that has been partially exposed by hair shaving. More specifically, light emitted by each of the first to third LEDs 211-213, i.e., the 310-nm light, the 320-nm light and the 330-nm light, was irradiated to each of 4 dogs (healthy beagles) at a dose of 300 mJ/cm² once every day for 4 days. On the fifth day, an allergen was intradermally injected in the irradiated and non-irradiated areas of each dog. The allergen was injected at a low or high concentration (10-6 g/mL or 10-5 g/mL of saline) in a volume of 0.05 mL.

The allergen used was polyoxyethylene hydrogenated castor oil 60 (HCO-60), which is used as a solubilizer for fat-soluble injectable solvents. It has been reported that when intravenously injected in dogs at 1.25 mg/kg or more, HCO-60 dose-dependently caused a decrease in blood pressure, flush, edema and itching, as well as an increase in plasma histamine concentration, and these reactions were suppressed by an anti-histamine (see Hisatomi A., et al., J. toxicol. sci., 18 (Suppl. 3), 1993). It has been also reported that intradermal injection of HCO-60 induced erythema and wheal reaction in dogs within 15 minutes after injection and mast cell degranulation was observed in the injection sites and that the erythema and wheal reaction was suppressed by an anti-histamine (Sugiyama Y., Kawarai S., et al., Vet. Dermatol., 27 (Suppl 1), 2016). Thus, HCO-60 can induce histamine-dependent allergic reaction.

In the tests, the results of which are shown in FIGS. 16(a), 16(b), and 17, the redness of the skin was calculated on the images of the irradiated and non-irradiated skin areas after intradermal injection of the allergen. FIGS. 16(a) and 16(b) show calculated values of redness of the skin after injection of the allergen, relative to a value of 1 for pre-injection, as mean values from 3 sites of each dog. In FIGS. 16(a), 16(b), and 17, statistical analysis was conducted using repeated measure analysis of variance followed by (if significant) Dunnett's t-test as a post hoc test. A p-value less than 0.05 indicates a significant difference between the groups compared. A significant difference in redness value between two groups means that allergic reaction (allergen-induced erythema and wheal reaction) is suppressed in the lower redness group, compared with the higher redness group.

As shown in FIGS. 16(a), 16(b), and 17, for injection of the allergen at the lower dose, the p-value of less than 0.01 in repeated measure analysis of variance indicates that there is a significant difference in values of redness between the non-irradiated area and at least one of the areas irradiated with the 310-nm light, the 320-nm light, or the 330-nm light. The p-values of less than 0.01 in the subsequent Dunnett's t-test indicate that there is a significant difference in redness between the non-irradiated area and any of the irradiated areas. On the other hand, for injection at the higher dose, the p-value is 0.18 in repeated measure analysis of variance and therefore there was no significant difference in redness between the non-irradiated and the irradiated areas. However, for injection at the higher dose, Dunnett's t-test reveals that the p-value is less than 0.05 for comparison between the non-irradiated area and the area irradiated with the 320-nm light.

As seen from the results mentioned above, irradiation with the 320-nm light has noticeable inhibiting effect on allergic reaction induced by the allergen at the lower dose, and moderate inhibiting effect on allergic reaction induced by the allergen at the higher dose. Irradiation with either of the 310-nm light or the 330-nm light has noticeable inhibiting effect on allergic reaction induced by the allergen at the lower dose. Thus, irradiation with any of the 310-nm light, the 320-nm light and the 330-nm light has a inhibiting effect on allergic reaction. In other words, the present treatment method using the animal phototherapeutic apparatus 1 can be expected to have a therapeutic effect on skin diseases associated with abnormal immune response in animals.

The reasons why irradiation with the 320-nm light causes less sunburn as shown in FIG. 15 may be as follows: It is known that the absorption peak of DNAs is around 260 nm, the absorption peak of proteins is around 280 nm, and the absorption spectra of DNAs and proteins extend up to near 320 nm. The epidermis (the outermost tissue layer of the skin) is thinner in carmines than in humans and the thickness of canine epidermis is about half of that of humans (0.2 mm, for example). Thus, ultraviolet light is easier to reach the dermis, and consequently cause DNA damage, in carmines than in humans. The 320-nm light includes a smaller amount of light absorbed by DNAs than the 310-nm light so that the 320-nm light does not cause DNA damage, and consequently does not cause sunburn even at a dose of 1,500 $mJ/cm^2$.

The reasons for the inhibiting effect on allergic reaction on its test as shown in FIGS. 16(a), 16(b), and 17 may be as follows: The irradiation with the 310-nm light, the 320-nm light or the 330-nm light causes a decrease in agents produced by epidermal keratinocytes and involved in an allergic reaction.

In certain guidelines for UV-B phototherapy, which is a method for the treatment of skin diseases including psoriasis and cutaneous allergy in humans, it is recommended that UV-B used have a peak wavelength in the range of 308-313 nm. It is believed that in human, light having a peak wavelength shorter than the said wavelength range can increase the risk of skin cancer, while light having a peak wavelength longer than the said wavelength range has significantly reduced therapeutic effect. The test results shown in FIGS. 16(a), 16(b), and 17 confirm that not only the 310-nm light, which has a peak wavelength in the range of 308-313 nm, but also the 320-nm light and the 330-nm light, which each have a peak wavelength longer than 313 nm, have an inhibiting effect on allergic reaction. It might be occurred because of the fact that the epidermis is thinner in dogs than in humans, even the 320-nm light and the 330-nm light reduce capillary dilation resulting from mast cell degranulation in the skin of dogs.

Gene Expression Analysis

Total RNAs were crudely extracted using RNAisoPlus (MACHEREY-NAGEL GmbH & Co.) according to the manufacturer's instructions from the punch skin biopsy samples that had been obtained from the irradiated and non-irradiated areas of the 3 dogs (dogs B, D and E) used in the allergic reaction inhibition tests before injection of the allergen, and then purified using NucleoSpin® RNA Clean-up XS (MACHEREY-NAGEL GmbH & Co.) according to the manufacturer's instructions.

RNA-seq analysis (TAKARA BIO Inc.) was conducted on the prepared total RNA using a NovaSeq system (Illumina, Inc). Information was analysed about only known genes.

Table 1 shows values obtained by calculating logarithmic transformation of the expression level (in FPKM; Fragments Per Kilobase of exon per Million mapped reads) of MrgprX2 in the irradiated area, divided by that in the non-irradiated area.

TABLE 1

| Expression level of MrgprX2 | | | | | | | | | | | | |
|---|---|---|---|---|---|---|---|---|---|---|---|---|
| 310-nm light | | | | 320-nm light | | | | 330-nm light | | | | |
| Dog B | Dog D | Dog E | AVE. | Dog B | Dog D | Dog E | AVE. | Dog B | Dog D | Dog E | AVE. | |
| −1.7 | −1.3 | 0.5 | −0.8 | −0.1 | −0.2 | −1.1 | −0.5 | 0.1 | −0.3 | −0.8 | −0.3 | |

As seen from the data shown in Table 1, irradiation with light having a peak wavelength at 310, 320 or 330 nm generally suppresses the expression level of MrgprX2.

The following results are taken into consideration that the gene expression analysis and the allergic reaction inhibition tests together with the facts that MrgprX2 is a target molecule of a factor promoting the degranulation response in mast cells (Tatemoto K. et al., Biochem. Biophys. Res. Commun., 2006, 349(4): 1322-1328), that the pseudo-allergic drug reactions disappear in the mice lacking MrgprB2, which is the mouse counterpart for MrgprX2 (McNeil B D. et al., Nature, 2015, 519(7542): 237-241), and that MrgprX2 expression is upregulated in skin tissues from human subjects with severe chronic urticaria (Fujisawa D. et al., J. Allergy Clin. Immunol., 2014, 134(3): 622-633). The inventors suggest the following mechanism for the treatment of allergic diseases with irradiation with light having a peak wavelength in the range of 305-335 nm, although not wishing to be bound by any theory: The light having a peak wavelength in the range of 305-335 nm suppresses MrgprX2 expression level in irradiated areas, thereby inhibiting the reaction of mast cells with an allergen(s) in the areas and therefore reducing the release of a bioactive factor(s) such as histamine.

It is also observed that in the irradiated areas, the expression levels of epidermal growth factors such as keratin and fibrillin (FBN2) are upregulated. This may suggest that light having a peak wavelength in the range of 315-335 nm may have no less therapeutic effect on skin wounds than light having a peak wavelength in the range of 305-315 nm.

In addition, it was observed that the expression levels of the following genes showed tendency to be upregulated by irradiation with the 310-nm light, the 320-nm light, or the 330-nm light:

Alkaline phosphatase, liver/bone/kidney (ALPL)
Collagen type VI alpha 5 chain (COL6A5): This is expressed in cells immediately above epidermal basal cells in humans. The gene expression disappears in patients with atopic dermatitis and therefore this gene is suggested to be associated with the pathological condition.
Matrilin (MATN3): This is involved in the formation of stromal networks in human skin dermis.
Serpin family E member 1 (SERPINE1): This is involved in the neogenesis of fibroblasts.
Agmatinase (AGMAT): This is involved in the control of viral infection.
MARCO (Macrophage receptor with collagenous structure): This is a scavenger receptor, which recognizes and internalizes foreign entities. It is expressed on macrophages and involved in the production of type I interferon, which is important for bacterial clearance.
Cardiomyopathy Associated 5 (CMYA5): This is a myofibroblast differentiation factor.
Troponin C1 and Troponin I1: This is a regulator of cardiomyocyte contraction. Therefore, it is thought to be involved in myofibroblast contraction in skin.

In addition, it was observed that the expression levels of the following genes showed tendency to be upregulated by irradiation with the 310-nm light:

Interleukin 17B (IL17B): This is a chemokine produced in fibroblasts and inducing cellular infiltration.
Interleukin 1 alpha (IL1A): This is an inflammatory cytokine and its production by epidermal keratinocytes is enhanced by UV irradiation.

In contrast, it was observed that the expression levels of the following genes showed tendency to be downregulated by irradiation with the 310-nm light, the 320-nm light, or the 330-nm light:

Interleukin 20 receptor subunit beta (IL-20RB)
Matrix metallopeptidase 1 (MMP1)

The upregulation of these gene expressions causes skin fibroblast damage and facilitates photoaging.

In addition, it was observed that the expression level of the following gene showed tendency to be downregulated by irradiation with the 310-nm light:

Mesoderm posterior bHLH transcription factor 1 (MESP1)

In particular, it was observed that the expression levels of the following genes showed tendency to be upregulated by irradiation with the 320-nm light:

Collagen type XIX alpha 1 chain (COL19A1): This is classified in Fibril associated collagens with interrupted triple helices (FACIT collagen) involved in skin proteoglycan. It is suggested that this is involved in the maintenance of skin tissue.
Myocyte enhancer factor-2 (MEF2C): This is involved in myocyte differentiation.
IL-26: This gene is involved in angiogenesis and therefore facilitates recovery from injury.

Based on the results mentioned above, it is believed that light of around 310 nm, light of around 320 nm, and light of around 330 nm (especially, light of around 320 nm and light of around 330 nm) facilitate the differentiation and/or neogenesis of myoblasts and/or blasts, thereby being involved in regeneration of skin. In addition, with light of around 320 nm, inflammatory reaction is inhibited compared to light of around 310 nm.

(Treatment Results of Canine Atopic Dermatitis)

Figure 18A:
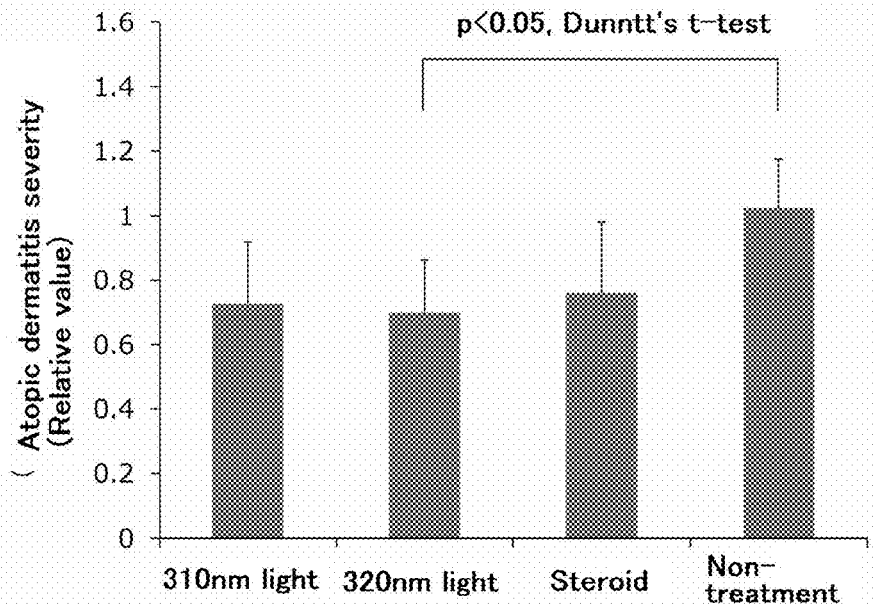
FIG. 18(a) shows the treatment effect of light having a peak wavelength in the range of 305 to 335 nm on allergic dermatitis.
Figure 18B:
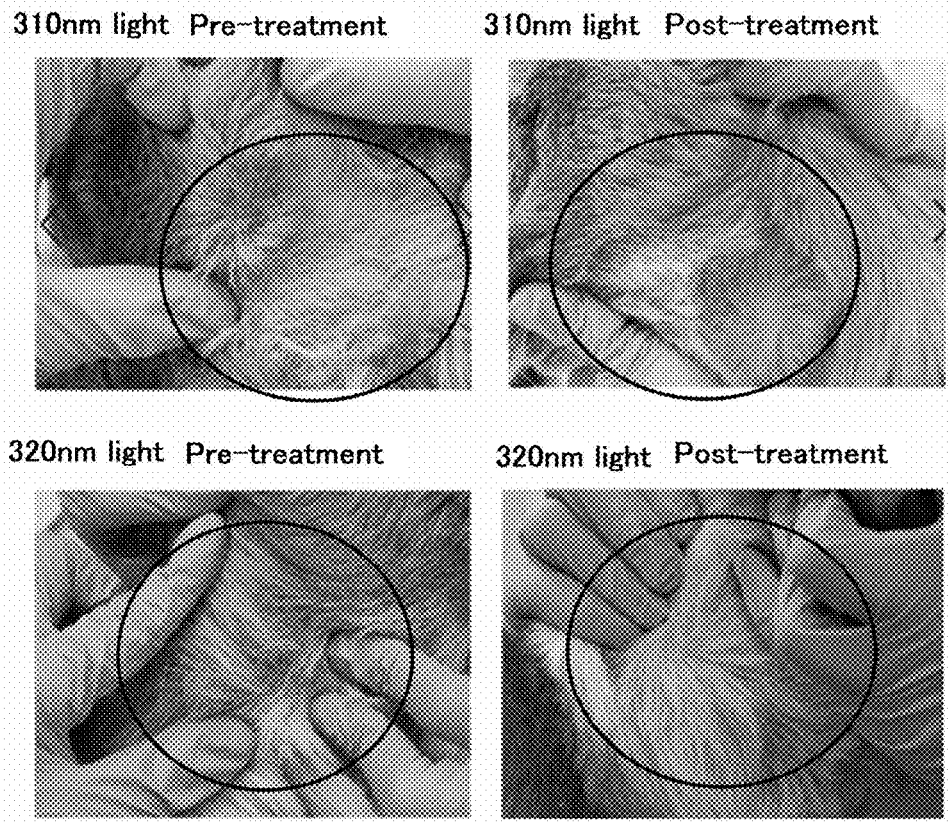
FIG. 18(b) shows changes by the treatments, of skin affected with allergic dermatitis.

FIG. 18(a) is a graph showing the treatment effect on atopic dermatitis in dogs, and FIG. 18(b) is a photograph showing a change of skin affected with atopic dermatitis by the treatment.

In five dogs (two beagles, one Yorkshire terrier, one toy poodle and one Pomeranian) diagnosed with canine atopic dermatitis and being symptomatic, the effectiveness of irradiation with light having a peak wavelength at 310 or 320 nm was examined by the double blind method. The irradiation was carried out by using the animal phototherapeutic apparatus 1.

Two skin areas to be irradiated with LED light, one skin area to be treated with an external preparation of steroid, and one untreated area were established in each case.

Treatment with LED light irradiation was carried out once a week. The dose was 300 mJ/cm$^2$ at the start. One week after each irradiation, it was checked that no adverse event including erythema had occurred and then the dose was increased by 100 mJ/cm$^2$. The treatment was continued for a total of 4 weeks and totally four of the treatments were carried out.

In the treatment with an external preparation of steroid, it was applied directly to the affected areas once a week for a total of 4 weeks. Totally, four of the treatments were carried out.

For evaluation of the effectiveness, the severity of atopic dermatitis was scored on the basis of the degrees of erythema, hair loss, lichenification and keratolysis in the areas of each dog.

FIG. 18(a) shows the treatment effects on canine atopic dermatitis. Severity scores (relative scores) after a lapse of the treatment period were calculated, relative to a severity score of 1 for the pre-treatment. The values indicated in the figure are the means and standard deviations of relative severity scores in each of five dogs.

As clearly seen in FIG. 18(a), atopic dermatitis was unchanged in the non-treated areas, while it was observed that atopic dermatitis was ameliorated in the areas treated with the 310-nm light, the 320-nm light or the external preparation of steroid, meaning that the treatment with the 310-nm light or the 320-nm light are no less effective on atopic dermatitis than the treatment with external preparation of steroid. Dunnett's t-test confirms that p-value is less than 0.05 only when the results of the irradiation treatment with the 320-nm light is compared to the results of non-treatment.

FIG. 18(b) shows photographs of affected skin area before and after the treatment with the 310-nm light or the 320-nm light and indicates that the treatments markedly ameliorated all of the symptoms: erythema, hair loss, lichenification and keratolysis.

The results mentioned above indicate that the present treatment method carried out using the animal phototherapeutic apparatus 1 can treat canine allergic dermatitis.
(Treatment Results of Cutaneous Lymphoma)

Figure 19:
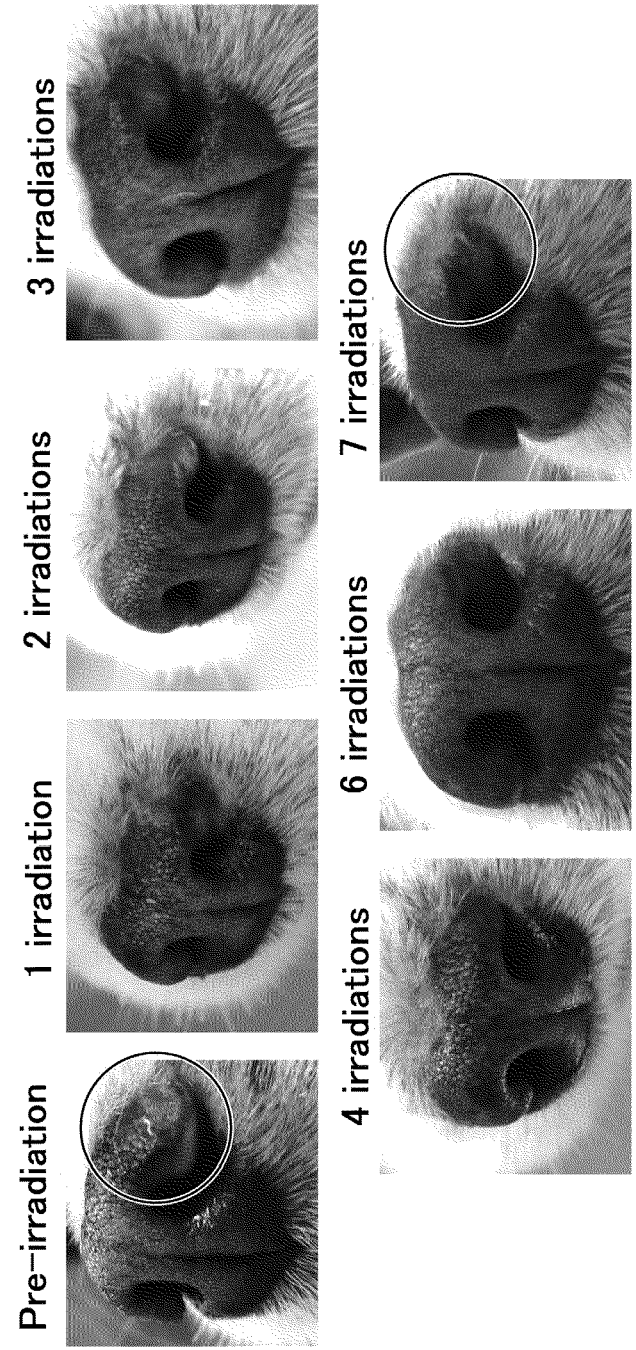
FIG. 19(a) shows the irradiation conditions for the treatment of cutaneous lymphoma.
FIG. 19(b) shows changes of skin affected with cutaneous lymphoma achieved by the treatments.

FIG. 19(a) illustrates the irradiation conditions for the treatment of cutaneous lymphoma and FIG. 19(b) shows a change of skin affected with cutaneous lymphoma, by the irradiation treatment.

The results of the treatment with the animal phototherapeutic apparatus 1 on cutaneous lymphoma will be described below with reference to FIGS. 19(a) and 19(b). More specifically, the results of the treatment with the animal phototherapeutic apparatus 1 on cutaneous lymphoma occurred in the nasal cavity of a chihuahua dog will be described below.

In this treatment, the affected area was irradiated with the 320-nm light once a week. After checking that no side reaction including erythema had occurred, the treatment was repeated while the dose was increased by 100 mJ/cm$^2$. More specifically, at the first time, the 320-nm light was irradiated at a dose of 300 mJ/cm$^2$, as shown in FIG. 19(a). More specifically, the 320-nm light was irradiated at an illuminance of 6.5 mW/cm$^2$ for 46 seconds.

At the second time to the sixth time, the 320-nm light was irradiated while the dose was increased by 100 mJ/cm$^2$ each time. More specifically, the light was irradiated at increasing doses of 400-800 mJ/cm$^2$. In other words, the light was irradiated for 62-123 seconds. At the seventh time, the light was irradiated at a dose of 800 mJ/cm$^2$ as at the sixth time.

As shown in FIG. 19(b), macroscopic observation in the partially gray-colored skin areas revealed a large number of depigmented (vitiligo) lesions with lymphocyte infiltration and inflammatory lesions in the left nasal cavity before irradiation ("pre-irradiation", in the circle). The lesions became smaller at each time of irradiation and macroscopically detectable depigmented lesions were ameliorated after the seventh irradiation ("post-7th irradiation", in the circle). Canine cutaneous lymphoma is an intractable disease, which is generally treated with an anti-cancer and dogs with which is believed to have a life expectancy of about 3 months. The photo-treatment of the disease with the animal phototherapeutic apparatus 1 may prevent worsening of the symptoms. It is confirmed that present treatment method carried out using the animal phototherapeutic apparatus 1 has a therapeutic effect on canine cutaneous lymphoma.
<Mechanisms>

Although not wishing to be bound by any theory, the present inventors believe that the mechanisms of the therapeutic effect on skin diseases provided by the light having a peak wavelength in the range of 315-335 nm are as follow:

Inflammatory skin diseases occur as a result of infiltration and migration of an excess amount of inflammatory cells (eosinophil, T lymphocytes, mast cells, neutrophil, basophil) in the epidermis and dermis.

Generally, narrowband ultraviolet B phototherapy for human using light having a peak wavelength in the range of 308-313 nm is believed to have an effect only on epidermis. Specifically, the large number of the inflammatory cells migrating in epidermis are killed to decrease in the number by damaging DNAs in inflammatory cells using light absorption by DNAs and by being exposed to singlet oxygen and reactive oxygen species generated from light absorption by proteins such as intercellular substances, especially aromatic amino acids. In the same way, the number of antigen-presenting cells (dendrite cells, monocytes, macrophages, B cells) in epidermis may be decreased and the amounts of the factors produced by keratinocytes and involved in allergic reactions are also decreased.

In addition, the light acts directly or indirectly on epidermal keratinocytes, antigen-presenting cells such as Langerhans cells, regulatory lymphocytes and mast cells present in the dermis, and fibroblasts to affects the signal transduction between the cells existing in the skin.

On the other hand, there is a concern that narrowband ultraviolet B phototherapy causes DNA damage also in normal cells. In especially dogs and cats with thinner epidermis, ultraviolet light easily reaches the dermis, thereby damaging DNAs in normal cells in epidermis and dermis, and in the worst case, there is a risk of developing skin cancer or the like.

The light having a peak wavelength in the range of 315-335 nm, used in embodiments of the present invention, is not significantly absorbed by DNA and therefore does not cause DNA damage, while singlet oxygen and reactive oxygen species, which are generated as a result from absorption of the UV light by proteins such as intercellular substances, reduce inflammatory cells and antigen-presenting cells, and other factors involved in allergic reactions in the epidermis.

It is also believed that some amount of the light having a peak wavelength in the range of 315-335 nm can reach the dermis, thereby reducing inflammatory cells and antigen-presenting cells, and other factors involved in allergic reactions also in the dermis.

In addition, it is believed that light having a peak wavelength in the range of 315-335 nm can directly or indirectly reduce mast cells, which are abundant in the dermis, or suppress the expression level of receptors for a factor promoting the degranulation response (MrgprX2, for example) in mast cells, thereby inhibiting the reaction between allergic substances and mast cells to decrease the release of bioactive substances such as histamine. As a result, allergic diseases can be treated with the light.

Various embodiments and variations have been described above, but the present invention may be configured as any combination of them.

Further, the present disclosure is not limited to the above-described embodiments, and can be implemented in various configurations without departing from the gist of the present disclosure.

In the present specification, a numerical range "a to b" or "a-b" ("a" and "b" represent specific numerical values) means a range between a and b, both inclusive, that is, it is used synonymously with a "range of a or more and b or less".

It is to be noted that the above embodiments and examples are given by way of illustration only for the purpose of better understanding of the invention. It is to be also understood that the present invention is not limited to the particular configurations, arrangements, process steps, means and devices described in the specification and the appended drawings.

A person skilled in the art can understand and easily recognize that various other changes, modifications and alterations of the concrete measures, means, and methods can be made to the embodiments described above without departing from the spirit and scope of the present invention. It is to be further noted that aspects of the present invention described with respect to one embodiment may be incorporated in a different embodiment although not specifically described relative thereto. That is, all embodiments and/or features of any embodiment can be combined in any way and/or combination.

All scientific literature and patent documents mentioned in the present specification are incorporated herein in its entirety by reference.

The contents of all patents, patent applications and references cited in the present specification are incorporated by reference herein in their entireties, as if fully and specifically set forth herein, to the fullest extent permitted by applicable law.

REFERENCE NUMERAL LIST

1: Animal phototherapeutic apparatus
10: Apparatus body
17: Switch
21: LED
30: Controller
211: First LED
212: Second LED
213: Third LED

The invention claimed is:

1. A method of treating a non-human animal subject, comprising:
performing a first step comprising irradiating an affected area of skin of the non-human animal subject with light having a first peak wavelength, which is in a range of 315-335 nm at a first irradiation dose; and
one or more days after the first step, performing a second step comprising irradiating the affected area of the skin with light having a second peak wavelength in the range of 315-335 nm at a second irradiation dose, wherein the second peak wavelength is shorter than the first peak wavelength.

2. The method according to claim 1, wherein:
the first peak wavelength is in a range of 325-335 nm, and
the second peak wavelength is in a range of 315-325 nm.

3. The method according to claim 1, wherein the light irradiated in the first and second steps has a relative illuminance at wavelengths less than 315 nm of 30% or less.

4. The method according to claim 1, wherein the method is used to treat a disease or disorder mediated by MrgprX2 gene.

5. The method according to claim 1, wherein the method is used to treat a disease or disorder selected from the group consisting of allergic dermatitis, cutaneous lymphoma, vitiligo, a wound, alopecia, an infectious disease, a skin abscess, and pyoderma.

6. The method according to claim 1, wherein the first step further comprises irradiating the affected area with the light having the first peak wavelength at a third irradiation dose that is higher than the first irradiation dose.

7. The method according to claim 6, wherein:
the first irradiation dose is 300 $mJ/cm^2$ or less, and
the third irradiation dose is more than 300 $mJ/cm^2$ but less than an irradiation dose that would cause sunburn to the skin.

8. The method according to claim 6, wherein the first step further comprises repeating the step defined in claim 6, with the third irradiation dose increasing each repetition.

9. The method according to claim 1, wherein the second step further comprises irradiating the affected area with the light having the second peak wavelength at a fourth irradiation dose that is higher than the second irradiation dose.

10. The method according to claim 9, wherein the second step further comprises repeating the step defined in claim 8, with the fourth irradiation dose increasing each repetition.

11. The method according to claim 1, further comprising performing a third step comprising irradiating the affected area with light having a third peak wavelength in a range of 305-315 nm at a fifth irradiation dose.

12. The method according to claim 11, wherein the third step further comprises irradiating the affected area with the light having the third peak wavelength at a sixth irradiation dose that is higher than the fifth irradiation dose.

13. The method according to claim 12, wherein the third step further comprises repeating the step defined in claim 11, with the sixth dose increasing each repetition.

14. The method according to claim 11, wherein the fifth irradiation dose is 300 $mJ/cm^2$ or less.

15. The method according to claim 1, wherein the light having a peak wavelength in the range of 315-335 nm is emitted by a light emitting diode (LED) or laser diode (LD).

* * * * *